(12) United States Patent
Luttrell et al.

(10) Patent No.: US 11,980,376 B2
(45) Date of Patent: May 14, 2024

(54) OSTEOTOMY GUIDE

(71) Applicant: Wright Medical Technology, Inc., Memphis, TN (US)

(72) Inventors: Paul Luttrell, Germantown, TN (US); Erin Muller, Fort Wayne, IN (US); Daniel E. Free, Oakland, TN (US); Joseph Ryan Woodard, Memphis, TN (US); Jesse G. Moore, Germantown, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 435 days.

(21) Appl. No.: 17/341,527

(22) Filed: Jun. 8, 2021

(65) Prior Publication Data

US 2021/0290251 A1 Sep. 23, 2021

Related U.S. Application Data

(63) Continuation of application No. 16/846,596, filed on Apr. 13, 2020, now Pat. No. 11,051,831, which is a
(Continued)

(51) Int. Cl.
*A61B 17/17* (2006.01)
*A61B 17/15* (2006.01)
(Continued)

(52) U.S. Cl.
CPC ........ *A61B 17/1775* (2016.11); *A61B 17/151* (2013.01); *A61B 17/1682* (2013.01);
(Continued)

(58) Field of Classification Search
CPC ...................... A61B 17/17–17/1775
See application file for complete search history.

(56) References Cited

U.S. PATENT DOCUMENTS

| 5,496,324 A | 3/1996 | Barnes |
| 5,562,674 A | 10/1996 | Stalcup et al. |

(Continued)

FOREIGN PATENT DOCUMENTS

| EP | 2997926 A1 | 3/2016 |
| JP | 2004275722 A | 10/2004 |

(Continued)

OTHER PUBLICATIONS

First Office Action issued in connection with corresponding Japanese Patent Application No. 2020-145939, 4 pages, dated May 24, 2022.
(Continued)

*Primary Examiner* — Zade Coley
(74) *Attorney, Agent, or Firm* — DUANE MORRIS LLP

(57) ABSTRACT

A guide for a bone cut comprises a guide base having an inner wall defining an opening. The inner wall has a plurality of detents distributed around the opening. The guide base has a proximal surface adapted to contact a skin of a person. An inner collar has one or more spring loaded devices extending outward from the inner collar in opposite directions. The inner collar is mountable with the spring loaded devices fitting within one or more of the plurality of detents. The inner collar has an inner wall defining a bore for receiving a cutting tool. The inner collar is configured to pivot the cutting tool about an axis, for cutting a bone. The axis lies along or parallel to a line along which the spring loaded devices lie.

8 Claims, 22 Drawing Sheets

Related U.S. Application Data continuation of application No. 16/100,308, filed on Aug. 10, 2018, now Pat. No. 10,653,432.

(51) Int. Cl.
| | |
|---|---|
| *A61B 17/16* | (2006.01) |
| *A61B 90/00* | (2016.01) |
| *A61B 90/11* | (2016.01) |
| *A61B 17/00* | (2006.01) |
| *A61B 17/56* | (2006.01) |
| *A61B 17/84* | (2006.01) |

(52) U.S. Cl.
CPC .............. *A61B 90/11* (2016.02); *A61B 90/39* (2016.02); *A61B 2017/00367* (2013.01); *A61B 2017/564* (2013.01); *A61B 2017/565* (2013.01); *A61B 17/848* (2013.01); *A61B 2090/034* (2016.02); *A61B 2090/3966* (2016.02)

(56) References Cited

U.S. PATENT DOCUMENTS

| | | | |
|---|---|---|---|
| 5,571,184 A * | 11/1996 | DeSatnick | ............ A61F 2/0805 403/368 |
| 6,298,262 B1 | 10/2001 | Franck et al. | |
| 7,374,563 B2 | 5/2008 | Roger et al. | |
| 7,572,258 B2 * | 8/2009 | Stiernborg | ............ A61B 17/15 606/79 |
| 8,475,463 B2 | 7/2013 | Lian | |
| 8,906,026 B2 | 12/2014 | Ammann et al. | |
| 9,351,780 B2 | 5/2016 | Arthur et al. | |
| 2003/0157457 A1 | 8/2003 | Blacklock | |
| 2003/0220646 A1 | 11/2003 | Thelen et al. | |
| 2009/0005814 A1 | 1/2009 | Miller et al. | |
| 2011/0106095 A1 | 5/2011 | Cross et al. | |
| 2011/0301652 A1 | 12/2011 | Reed et al. | |
| 2012/0078252 A1 | 3/2012 | Huebner et al. | |
| 2012/0089192 A1 | 4/2012 | Biedermann | |
| 2012/0253410 A1 | 10/2012 | Taylor et al. | |
| 2013/0012945 A1 | 1/2013 | Chreene et al. | |
| 2013/0289399 A1 | 10/2013 | Choi et al. | |
| 2014/0163570 A1 | 6/2014 | Reynolds et al. | |
| 2014/0243828 A1 | 8/2014 | Heiney | |
| 2017/0348008 A1 | 12/2017 | Lavallee et al. | |
| 2018/0168682 A1 * | 6/2018 | Hazard, III | ............ A61B 34/20 |

FOREIGN PATENT DOCUMENTS

| | | |
|---|---|---|
| JP | 2010510032 A | 4/2010 |
| JP | 2014514024 A | 6/2014 |
| WO | 2005082259 A1 | 9/2005 |
| WO | 2008064211 A1 | 5/2008 |

OTHER PUBLICATIONS

Extended European Search Report issued in connection with corresponding European Patent Application No. 21174139.2, 8 pages, dated Aug. 16, 2018.

First Examination Report issued in connection with corresponding Australian Patent Application No. 2018229514, 8 pages, Apr. 30, 2018.

Partial Search Report issued in connection with corresponding European Patent Application No. 18197129.2, 14 pages, dated Apr. 11, 2019.

Extended European Search Report issued in corresponding European Patent Application No. 18197129.2, dated Jul. 19, 2019, 12 pages.

First Office Action issued in connection with corresponding Japanese Patent Application No. 2018-176334, dated Dec. 3, 2019, 5 pages.

* cited by examiner

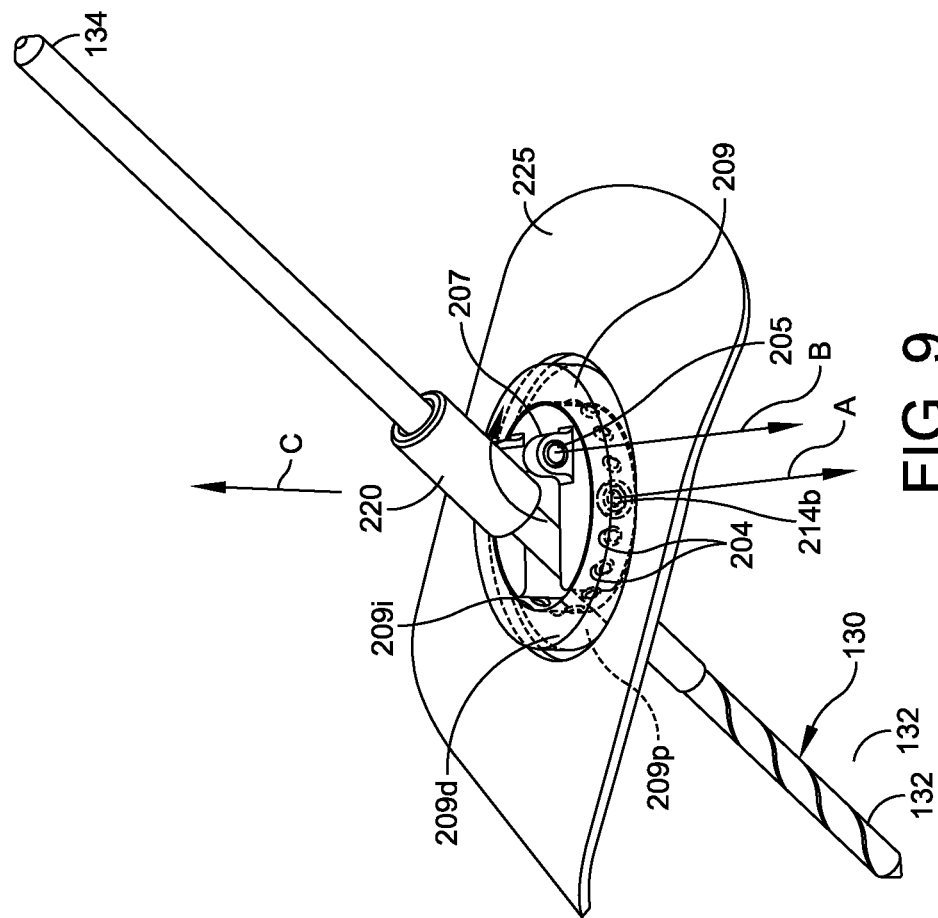
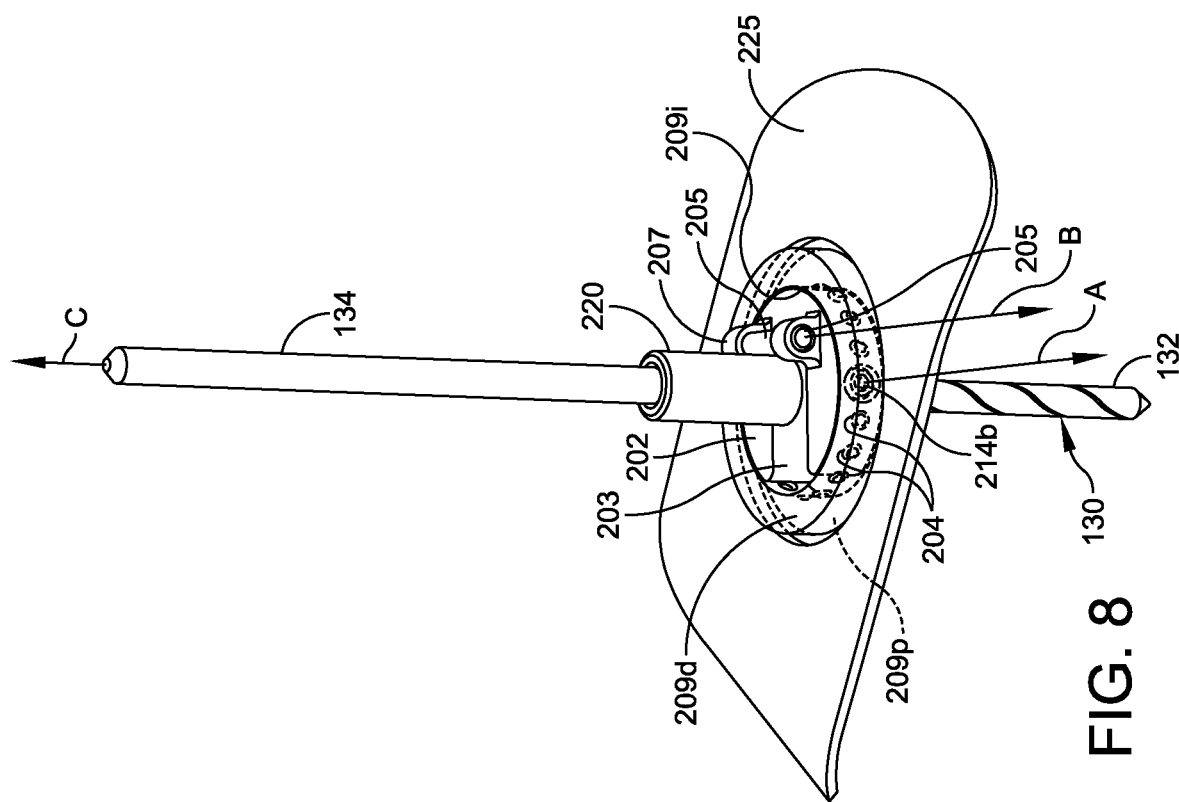
FIG. 8
FIG. 9

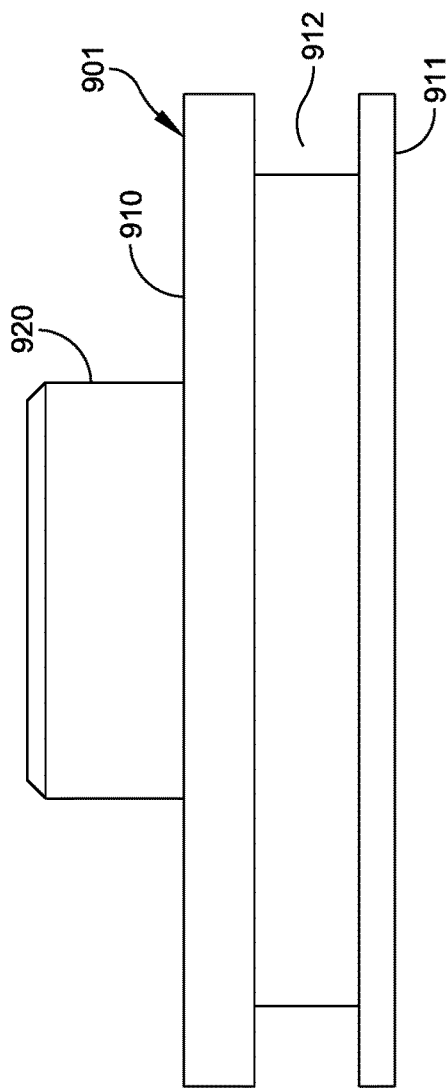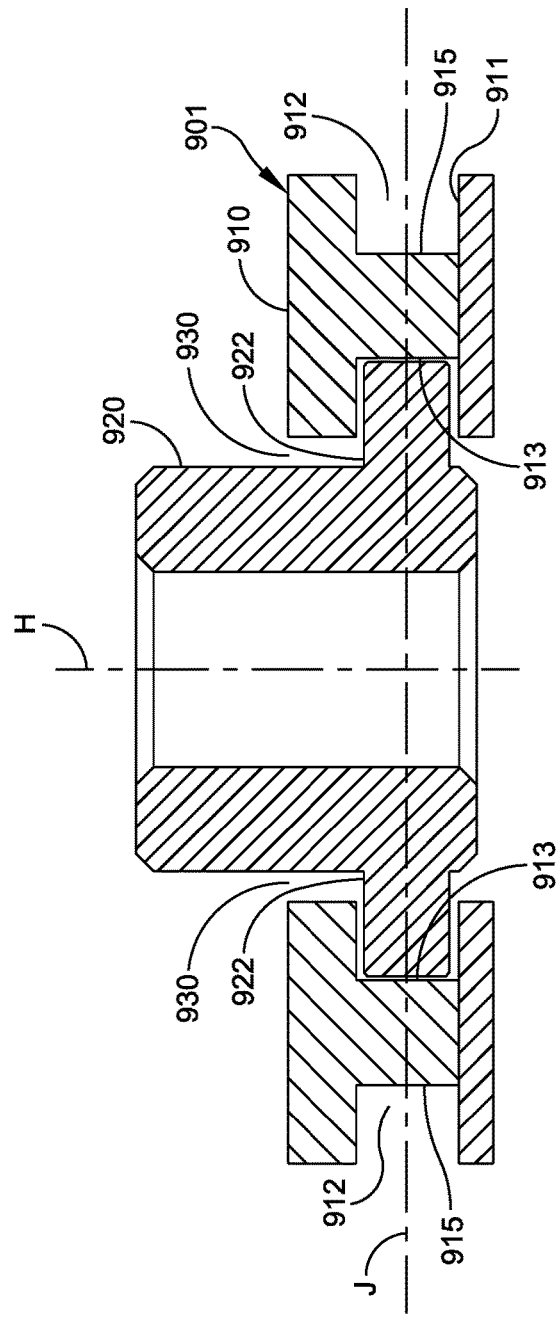

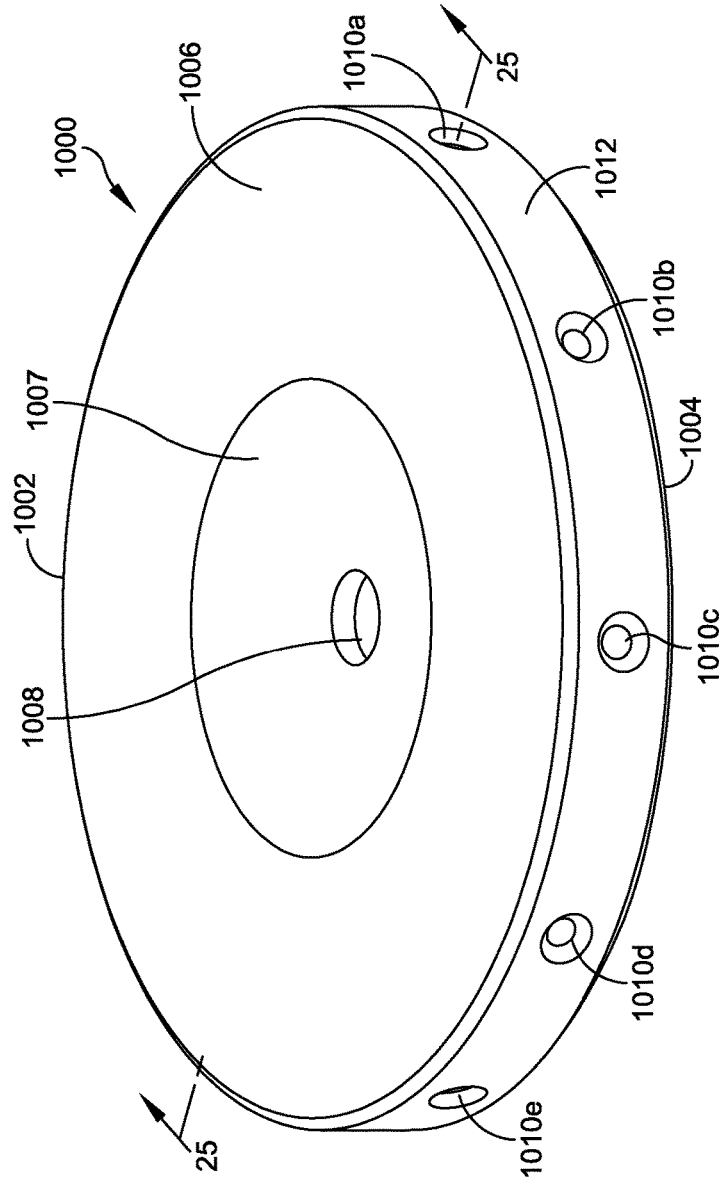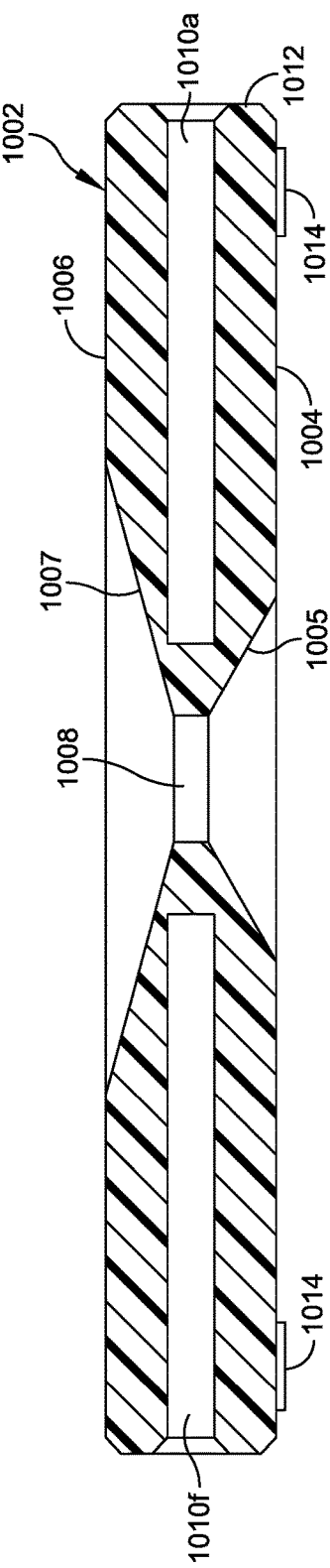

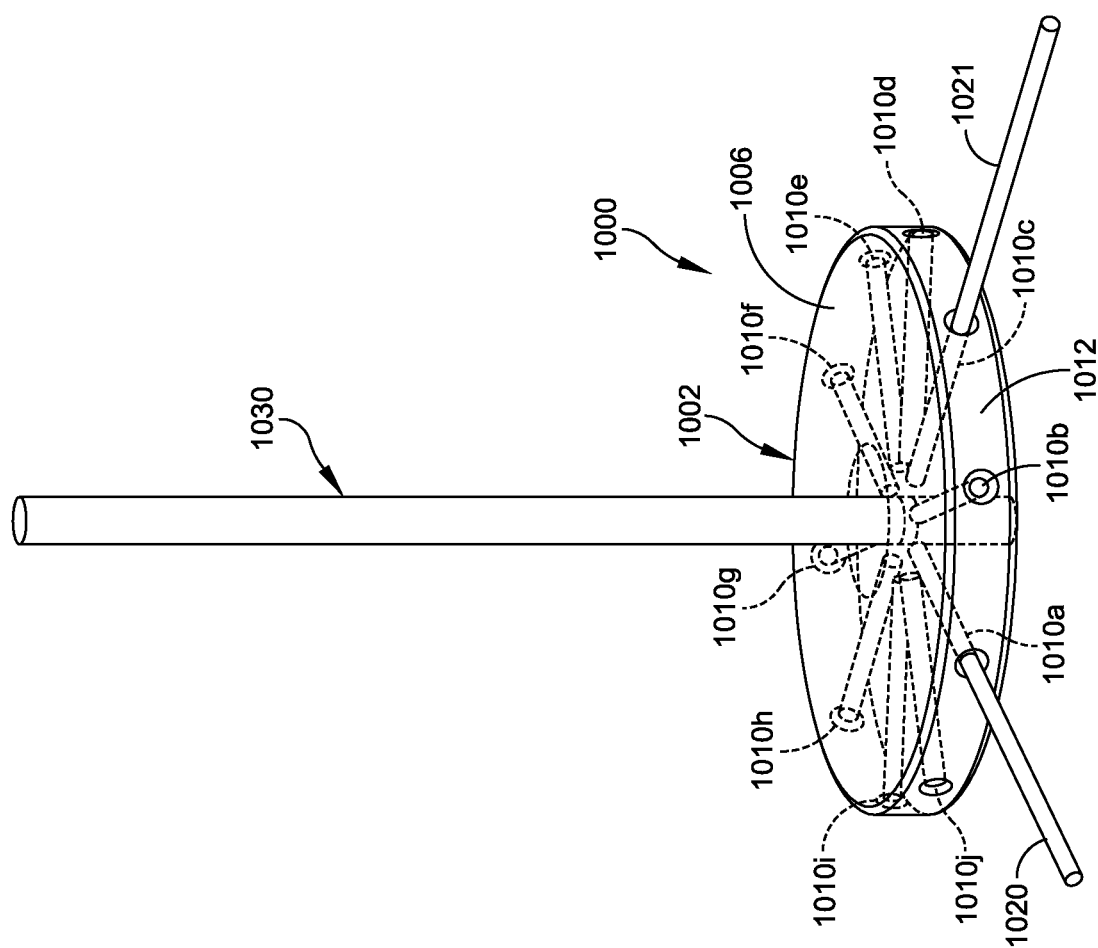

OSTEOTOMY GUIDE

CROSS REFERENCE TO RELATED APPLICATION

This application is a continuation of U.S. patent application Ser. No. 16/846,596, filed Apr. 13, 2020, which is a continuation of U.S. patent application Ser. No. 16/100,308, filed Aug. 10, 2018 (now U.S. Pat. No. 10,653,432), the entireties of which are incorporated by reference herein.

FIELD

This disclosure relates generally to medical devices and more specifically to guides for osteotomies.

BACKGROUND

Hallux valgus ("bunion") results from medial deviation of the first metatarsal of the foot. When the deviation is severe, corrective surgery involving an osteotomy may be performed. The plane of the osteotomy is defined by the entry cut of the cutting tool (e.g., a burr) into the metatarsal. From this entry cut the surgeon makes dorsal and plantar limbs of a chevron cut. The first entry of the burr creates the apex of the chevron. The surgeon works with care to ensure that the incision avoids damage to nerves, connective tissue, and the blood supply of the metatarsal. Minimally invasive surgical techniques may reduce collateral tissue damage and scarring, and reduce recovery time relative to open surgical methods.

SUMMARY

In some embodiments, a guide for a bone cut comprises a guide base having an inner wall defining an opening. The inner wall has a plurality of detents distributed around the opening. The guide base has a proximal surface adapted to contact a skin of a person. An inner collar has one or more spring loaded devices extending outward therefrom in opposite directions. The inner collar is mountable with the spring loaded devices fitting within one or more of the plurality of detents. The inner collar has an inner wall defining a bore for receiving a cutting tool. The inner collar is configured to pivot the cutting tool about an axis, for cutting a bone. The axis lies along or parallel to a line along which the spring loaded devices lie.

In some embodiments, a guide for a bone cut comprises a guide base having an inner wall defining an opening. The guide base has a proximal surface adapted to contact a skin of a person. An inner collar has an outer surface. The inner collar has an inner wall defining a bore for receiving a cutting tool. The inner collar is configured to pivot the cutting tool about a pivot axis of the guide, for cutting a bone. One of the inner wall of the guide base or the outer surface of the inner collar has one or more detents distributed thereon. The other of the inner wall of the guide base or the outer surface of the inner collar has one or more coupling mechanisms extending therefrom in opposite directions. The inner collar is mountable so that the one or more coupling mechanisms fit within two of the plurality of detents, and the coupling mechanisms are located along or parallel to the pivot axis.

In some embodiments, a guide for cutting a bone comprises a body having a proximal surface adapted to contact a skin of a person. A distal surface is opposite the proximal surface. The distal surface has one or more distal channels. Each distal channel has a respective longitudinal axis forming an oblique angle with the distal surface. Each distal channel has a bottom surface extending partially around the respective longitudinal axis thereof. Each distal channel extends from the bottom surface to the distal surface, so each distal channel has a varying depth. A central bore extends through the body, from the proximal surface to the respective bottom surface of each respective distal channel. The central bore is adapted to receive a drilling or cutting tool therethrough.

In some embodiments, a guide for an osteotomy comprises a circular body. A first arm and a second arm extend radially away from the circular body. At least one of the first arm or second arm is movable relative to the other of the first arm or second arm to vary an angle between the first arm and the second arm. A sleeve is concentrically arranged inside the body. The sleeve has an inner surface defining a bore through the sleeve. The bore is adapted to receive a cutting or grinding tool therethrough.

In some embodiments, a guide for cutting a bone comprises a cylindrical body having a proximal surface adapted to contact a skin of a person. The proximal surface has a proximal chamfer at a center thereof. A distal surface is opposite the proximal surface. The distal surface has a distal chamfer at a center thereof. The cylindrical body has an inner wall defining a central longitudinal bore extending through the body from the proximal chamfer to the distal chamfer. The central bore is adapted to receive a drilling or cutting tool therethrough. The cylindrical body has a circumferential surface with a plurality of radial bores extending inward from the circumferential edge. The radial bores are adapted to receive fixation elements therein.

In some embodiments, a method comprises selecting a guide having a predetermined chevron angle from among a plurality of guides having a plurality of respective chevron angles. The selected guide has a proximal surface and a distal surface. The distal surface has one or more channels. Each of the one or more channels has a longitudinal axis arranged at an oblique angle relative to the distal surface. The guide has a respective marker on the distal surface opposite each of the one or more channels. The proximal surface of the selected guide is adhered to a skin of a patient. A cutting tool is inserted into a central bore, where each of the one or more channels extends radially from the central bore. The marker is aligned opposite the selected channel with a direction of a cut. The cutting tool is tilted toward the selected channel.

BRIEF DESCRIPTION OF THE DRAWINGS

FIG. 8 is an isometric view of the guide of FIG. 7, showing the guide base rotated relative to the plate and with a cutting tool inserted through the sleeve.

FIG. 9 is an isometric view of the guide of FIG. 8, showing the sleeve and tool tilted away from the normal axis.

FIG. 22 is a side view of the body and sleeve of the guide of FIG. 19.

FIG. 23 is a cross section of the body, taken along section line 23-23 of FIG. 20.

FIG. 24 is an isometric view of a guide.

FIG. 25 is a cross section of the guide of FIG. 24, taken along section line 25-25.

FIG. 27 is an isometric view of the guide of FIG. 26, with a cutting tool inserted through the central longitudinal bore.

DETAILED DESCRIPTION

Figure 1:
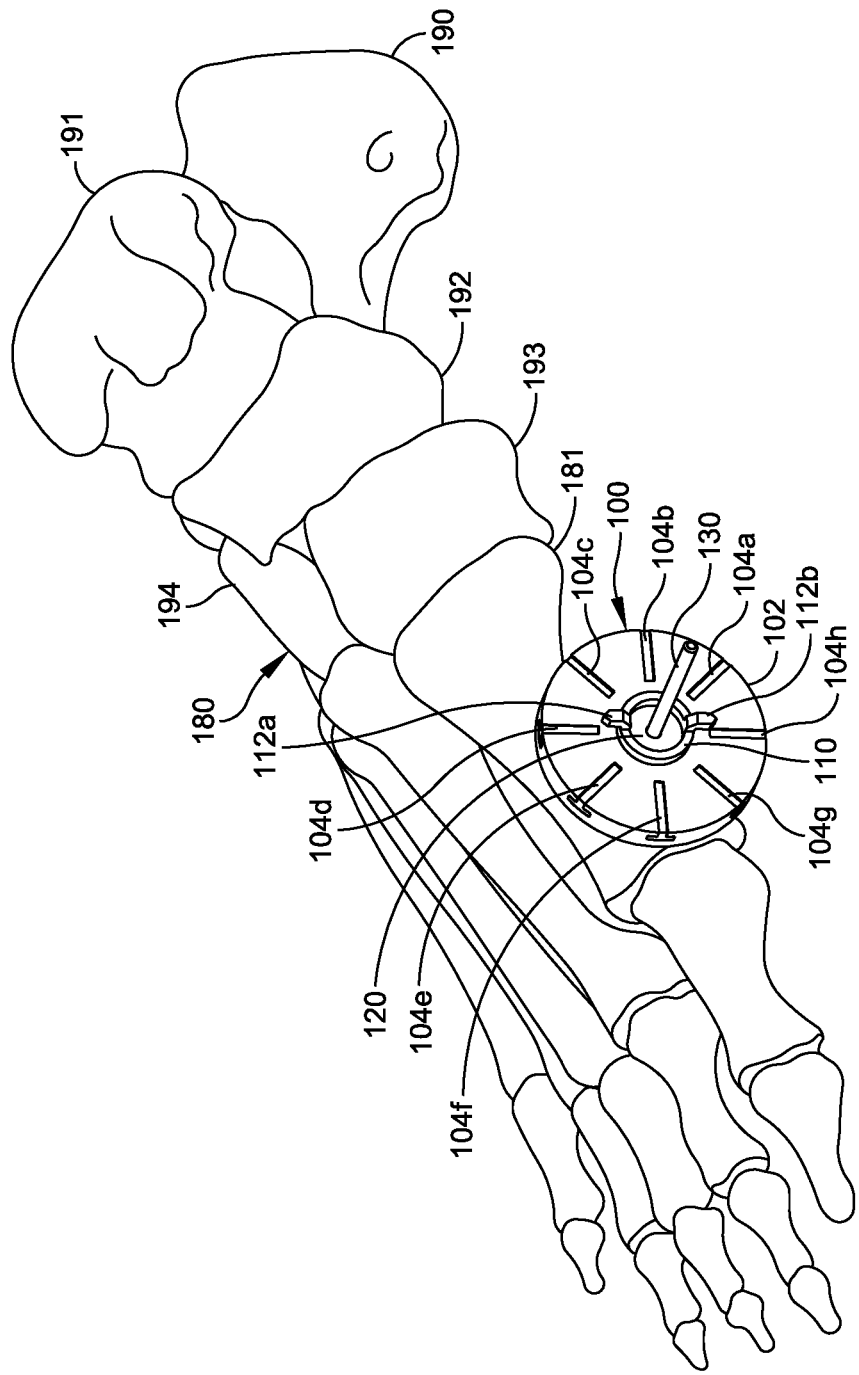
FIG. 1 is an isometric view of a foot with an embodiment of a guide adhered thereto.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, couplings, and the like, such as "connected" and "interconnected," refer to a relationship wherein structures are secured or attached to one another either directly or indirectly through intervening structures, as well as both movable or rigid attachments or relationships, unless expressly described otherwise.

This disclosure provides a cutting or drilling guide to simplify and streamline a minimally invasive surgery (MIS) technique while also providing reproducible results. The cutting or drilling guide may be used for guiding a burr, for example. In some embodiments, the cutting or drilling guide includes at least one disposable portion that can be cut or abraded during use. In some embodiments, the guide is configured to be attached to the skin of the patient using an adhesive, near the wound site. The cutting or drilling guide may include a pressure-sensitive adhesive for attaching the guide to the patient's skin (e.g., on the foot). The guide is placed over the osteotomy site and adhered to the patient's skin. The guide has a bore that accepts the associated cutting/drilling instrument. In some embodiments, the guide has a pivot axis for constraining the range of motion of the cutting/drilling instrument. This can prevent the cutting/drilling instrument from damaging the patient's skin near the bore.

FIGS. 1-6 show an embodiment of a guide 100 suitable for minimally invasive surgery. The guide 100 orients a surgical tool 130 for making one or more bone cuts. The tool 130 can have a shaft 134 having a portion 132 with cutting, grinding or polishing features. FIG. 1 shows the guide 100 adhered to the foot 180 of a patient. The skin and soft tissue are omitted from FIG. 1 for ease of viewing. The foot 180 includes the calcaneus 190, talus 191, navicular 192, cuneiform 193, cuboid 194, and a first metatarsal 181. The guide may be attached to this area of the patient's anatomy. In some embodiments, the guide 100 is adhered to the skin. For example, in a disk-shaped embodiment as shown in FIGS. 1-6, it may be easier to adhere the guide 100 to the skin without opening up the incision. In other embodiments, the guide 100 can be adhered to the bone itself. In some embodiments, the guide is attached using an adhesive. In some embodiments, the adhesive is applied around the periphery (near the circumference) of the guide 100, so the guide can be adhered to the skin around the incision without adhering to internal tissue.

In some embodiments, the guide 100 for a bone cut comprises a guide base 102 having an inner wall 103 defining an opening. The guide base 102 has a proximal surface 102p adapted to contact the skin of a person. An inner collar 120 has an outer surface 120s (best seen in FIG. 6). The inner collar 120 has an inner wall 120b defining a bore for receiving a cutting tool 130. The inner collar 120 is configured to pivot the cutting tool 130 about a pivot axis A of the guide 100, for cutting a bone. One of the inner wall 103 of the guide base 102 or the outer surface 120s of the inner collar 120 has a plurality of detents 116a-116h distributed thereon. The other of the inner wall 103 of the guide base 102 or the outer surface 120s of the inner collar 120 has a pair of coupling mechanisms (e.g., compression-driven coupling mechanisms, such as spring loaded devices, which can include ball plungers, blade plungers, springs, or the like) 114a, 114b extending therefrom in opposite directions. The inner collar 120 is mountable so that the pair of compression-driven coupling mechanisms, such as spring loaded devices 114a, 114b fit within two of the plurality of detents 116a-116h, and the pair of compression-driven coupling mechanisms, such as spring loaded devices 114a, 114b, are located along or parallel to the pivot axis A.

Figure 2A:
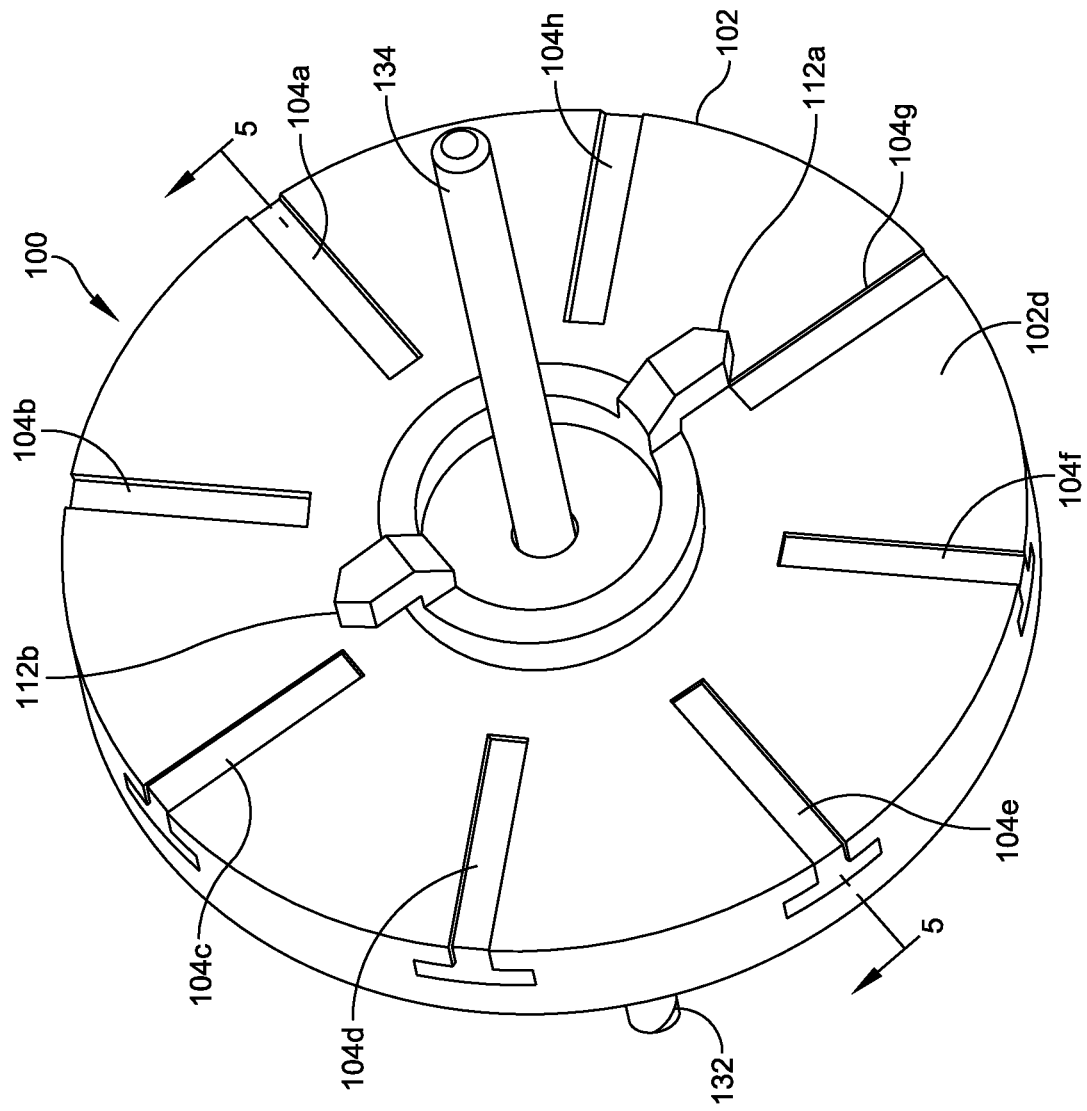
FIG. 2A is an isometric view of the guide of FIG. 1.
Figure 2B:
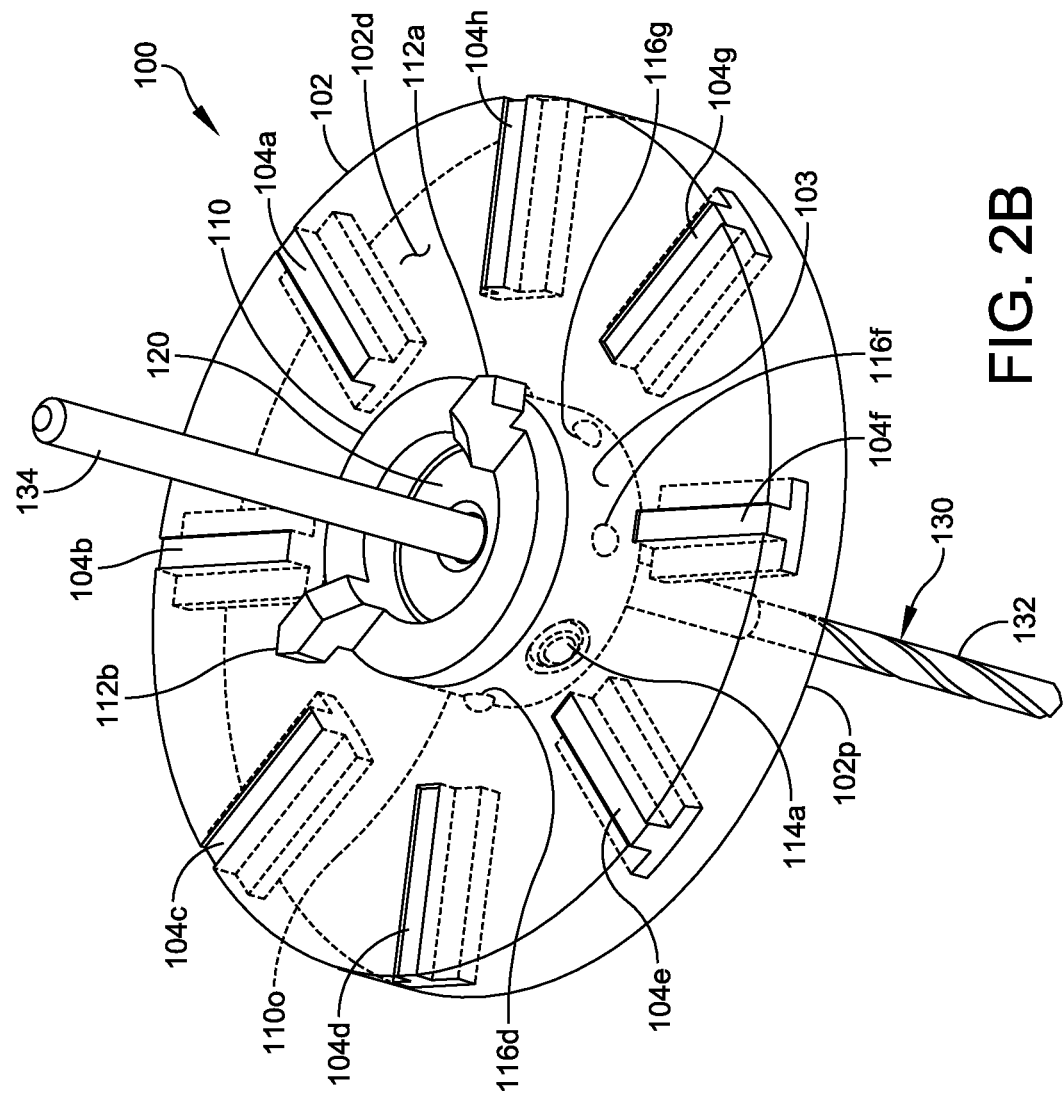
FIG. 2B shows the guide of FIG. 1, with hidden features indicated by dashed lines.
Figure 3:
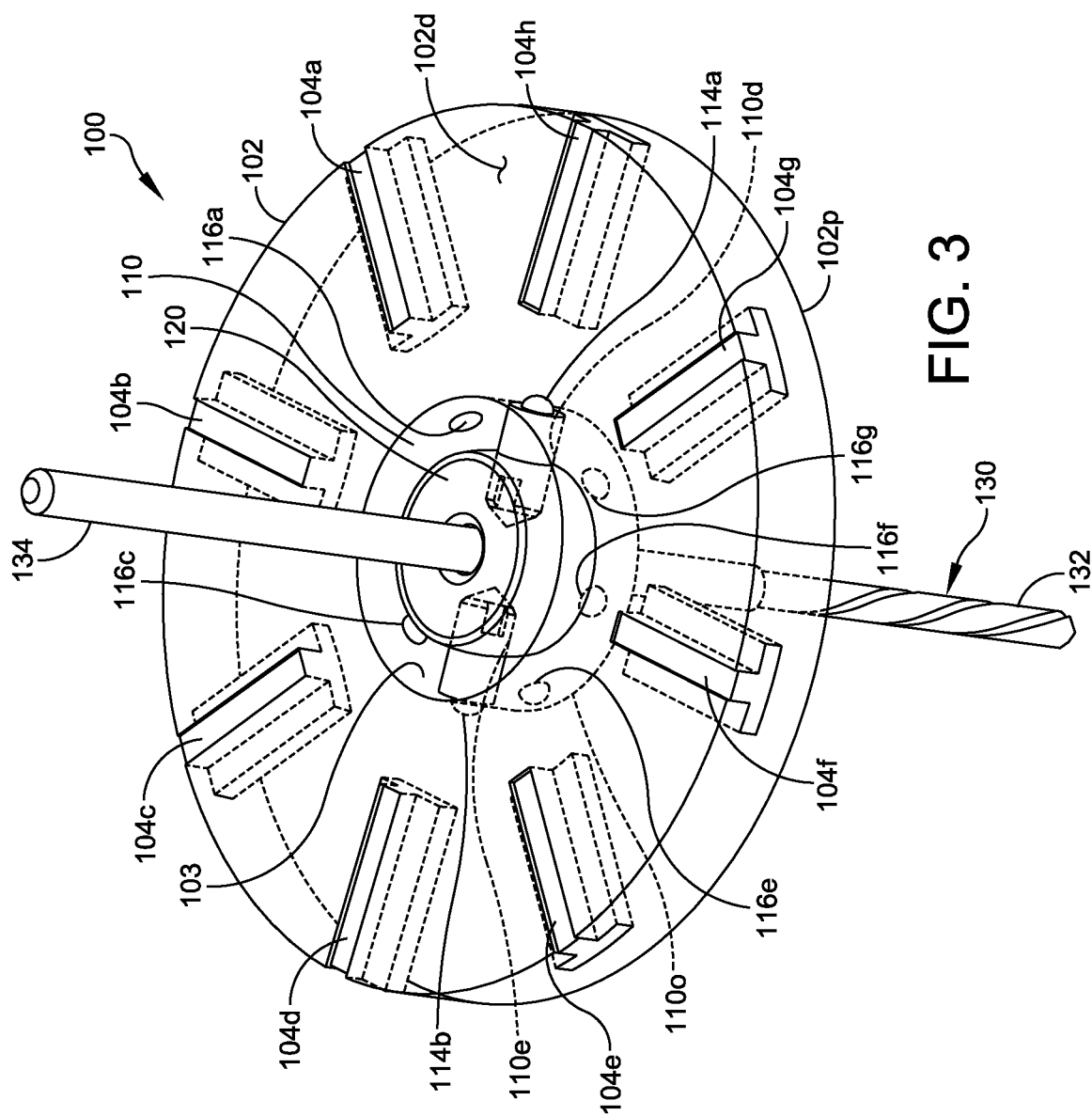
FIG. 3 shows the guide of FIG. 2B, rotated 90 degrees from the position of FIG. 2B and with a cutting tool inserted.
Figure 4:
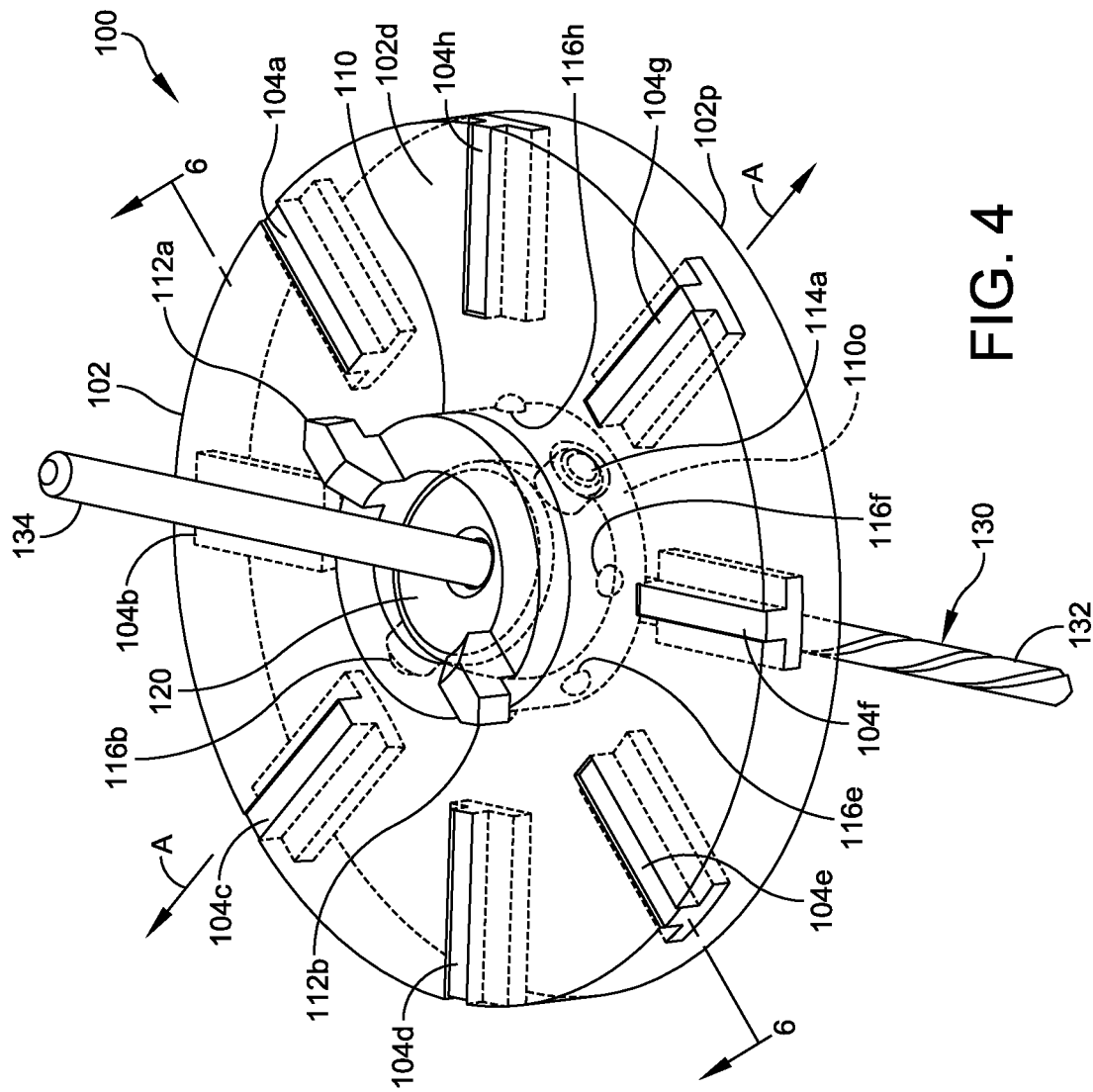
FIG. 4 shows the guide of FIG. 2B with the cutting tool tilted.

FIG. 2A is an isometric view of the guide 100 of FIG. 1. FIGS. 2B, 3 and 4 are additional isometric views of the guide 100, in which features hidden by the surface of the guide base 102 are indicated by dashed lines. The guide 100 includes a guide base 102 having an inner wall 103 defining an opening, as shown in FIG. 2B. The inner wall 103 has a plurality of detents 116a-116h distributed around the opening. The guide base 102 has a proximal surface 102p adapted to contact the skin of a person, adjacent to a wound site. An inner collar 120 has a pair of spring loaded devices (e.g., ball plungers or blade plungers) 114a, 114b extending outward in opposite directions from the inner collar 120, as shown in FIGS. 2B to 5. The inner collar 120 is mountable with the balls or blades of a pair of compression-driven coupling mechanisms, such as spring loaded devices (e.g., ball plungers 114a, 114b or blade plungers) fitting within two of the plurality of detents 116a, 116e on opposite sides of the inner wall 103 from each other. Some embodiments further comprise an outer sleeve 110 rotatably mounted within the opening defined by the inner wall 103 of the guide base 102. The outer sleeve 110 has an inner surface 110b, 110c, an outer surface 110o, and a pair of apertures 110d, 110e extending from the inner surface 110b to the outer surface 110o.

Figure 5:
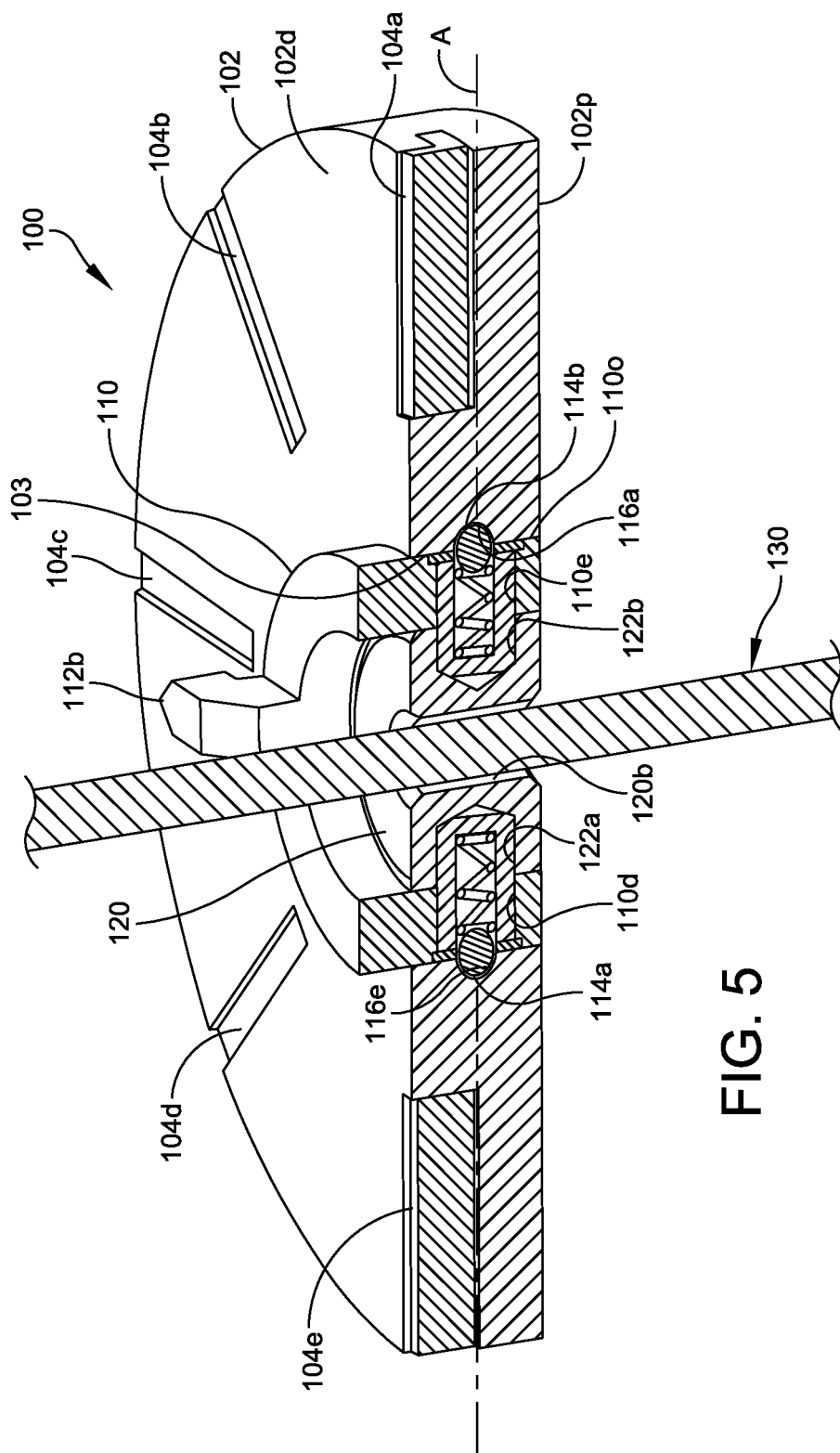
FIG. 5 is a cross section of the guide, taken along section line 5-5 of FIG. 2A.
Figure 6:
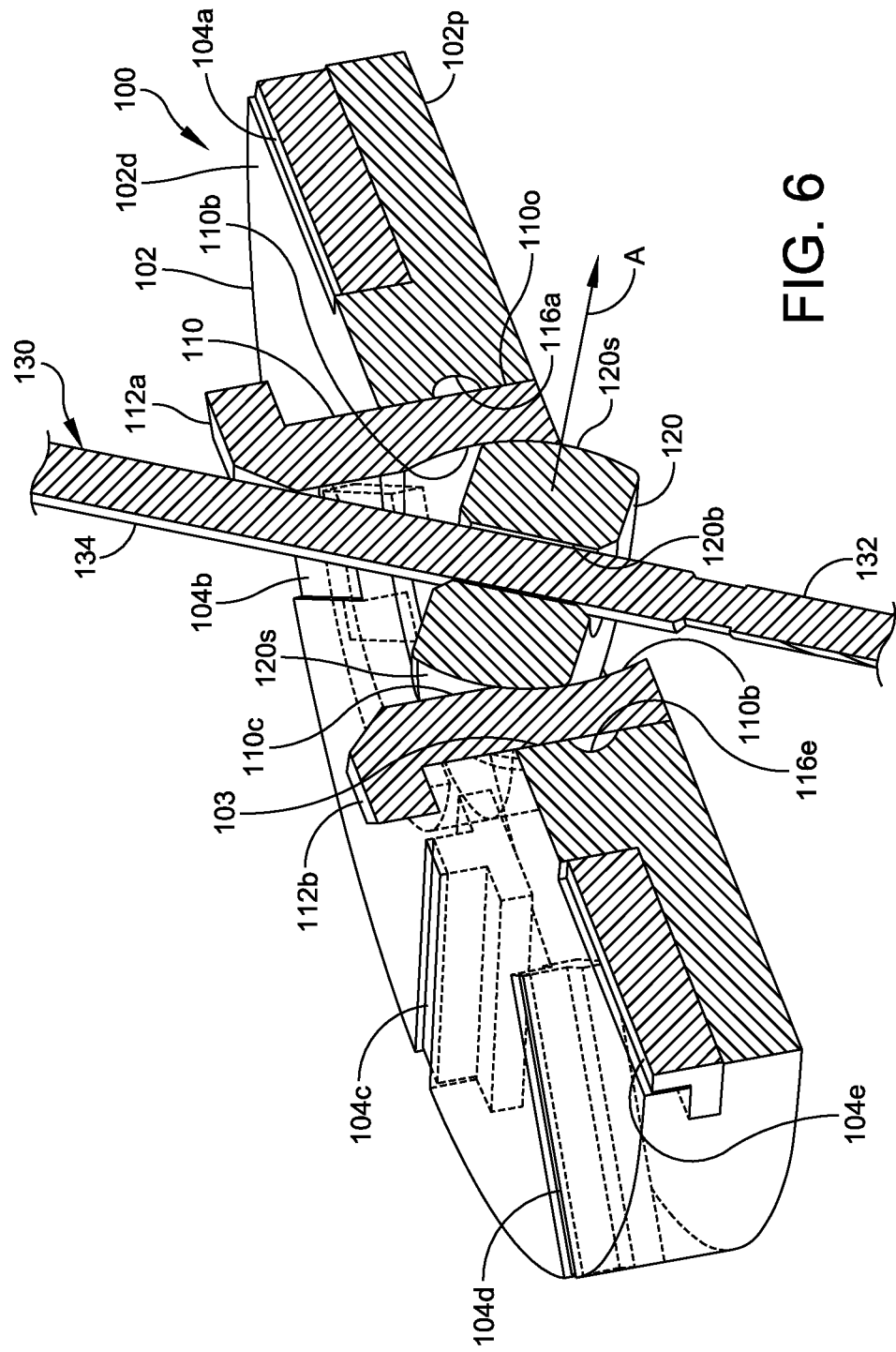
FIG. 6 is a cross section of the guide, taken along section line 6-6 of FIG. 4.

The inner collar 120 is best seen in FIGS. 3-6. FIG. 3 is an isometric view in which features hidden by the guide base 102 or outer sleeve 110 are indicated by dashed line. The inner collar 120 is pivotally mountable in the outer sleeve 110 with the pair of compression-driven coupling mechanisms, such as spring loaded devices (e.g., ball plungers 114a, 114b or blade plungers) 114a, 114b extending through the apertures 110d, 110e of the outer sleeve 110. In some embodiments, the inner surface 110b, 110c of the outer sleeve 110 includes a spherical concavity 110b and a cylindrical portion 110c, as best seen in FIG. 6. The inner collar 120 has a spherical outer edge 120s (best seen in FIG. 6) adapted to rotate within the spherical concavity 110b when the inner collar 120 pivots about the compression-driven coupling mechanisms, such as spring loaded devices (e.g., ball plungers or blade plungers) 114a, 114b. FIG. 4 is an isometric view of the guide 100 with the inner collar 120 rotated to pivot the cutting tool 130, where hidden details of the inner collar 120 are indicated by dashed lines.

The inner collar 120 has an inner wall 120b (best seen in FIGS. 5-6) defining a bore for receiving a cutting tool 130. The inner collar 120 is configured to pivot the cutting tool 130 about an axis A (FIGS. 4-6), for cutting a bone (e.g., bone 181). The axis A coincides with a line along or parallel to a central longitudinal axis of the spring loaded devices (e.g., ball plungers or blade plungers) 114a, 114b lie.

In some embodiments, the outer sleeve 110 has at least one projection 112a, 112b extending from a distal surface 102d of the guide base 102, opposite the proximal surface 102p of the guide base 102. The projections 112a, 112b can be angularly positioned so that at least a portion of each angular projection 112a, 112b is midway between the pair of apertures 110d, 110e (through which the spring loaded devices (e.g., ball plungers or blade plungers) 114a, 114b extend). In the example shown in FIGS. 2B, 4 and 5, the centerline of each projection 112a, 112b is midway between the pair of apertures 110d, 110e. In some embodiments, the at least one projection 112a, 112b is configured to act as a stop for pivoting by the cutting tool 130. The inner sleeve 120 can pivot about axis A (which extends through the centerlines of the spring loaded devices 114a, 114b) until the cutting tool 130 contacts one of the projections 112a, 112b, as shown in FIG. 6.

The inner collar 120 allows rotation of the cutting tool 130 (e.g., burr) for performing the cuts. The outer sleeve 110 acts as a "burr block" by limiting the range of pivot the cutting instrument 130 can achieve (as best seen in FIG. 6). The inner collar 120 and outer sleeve 110 can be formed as an over-molded two-part component. For example, the inner collar 120 may be a metal substrate machined from steel or aluminum and the metal substrate can be inserted into an injection molding tool for molding the outer sleeve 110 onto or around the metal substrate. The outer sleeve can comprise a thermoplastic elastomer, such as a styrenic, copolyester, polyurethane, polyolefin, or polyamide.

In some embodiments, the guide base 102 comprises a radiolucent material to allow visibility under fluoroscopy. In some embodiments, the guide base 102 has at least one radiopaque marker 104a-104h on a distal surface 102d opposite the proximal surface 102p. At least one radiopaque marker (e.g., 104a, 104e) can be angularly positioned midway between two detents 116a, 116e in the plurality of detents 116a-116h, so that the at least one radiopaque marker (e.g., 104a, 104e) is positioned to lie in a plane through which the cutting tool 130 pivots. The exemplary radiopaque markers 104a-104h have a T-shaped cross section for retaining the markers within respective T-shaped openings. In other embodiments (not shown), the radiopaque markers can have a different cross sectional shape (e.g., a dove tail shape), and the guide base 102 has correspondingly shaped grooves for receiving the radiopaque markers.

The radiopaque markers 104a-104h can be used to identify the trajectory of each cut. For example, the guide 100 can be positioned so that one or more of the markers 104a-104h align with standard osteotomy cuts (for example a chevron osteotomy). The bore 120b of the inner collar 120 is located at the apex of the chevron, and two of the radiopaque markers identify the plane of the associated dorsal and plantar cuts). In the example of FIGS. 1-6, there are eight markers 104a-104h evenly spaced 450 apart, allowing a chevron angle that is a multiple of 45°. Other embodiments can have a different number of markers (e.g., six or ten). Other embodiments can have unevenly spaced markers.

The radiopaque markers 104a-104h can also be used for other procedural osteotomy cuts, such as a calcaneal osteotomy, Weil osteotomy, distal metatarsal minimally invasive osteotomy (DMMO), or the like.

The spring loaded devices (e.g., ball plungers or blade plungers) 114a, 114b can include a cylinder having a ball at one end thereof, where the ball is biased by a spring to push toward the one end of the cylinder. FIG. 5 is a cross sectional view of the guide 100 taken along the axis A, which extends through the centers of the spring loaded devices 114a, 114b.

Figure 7:
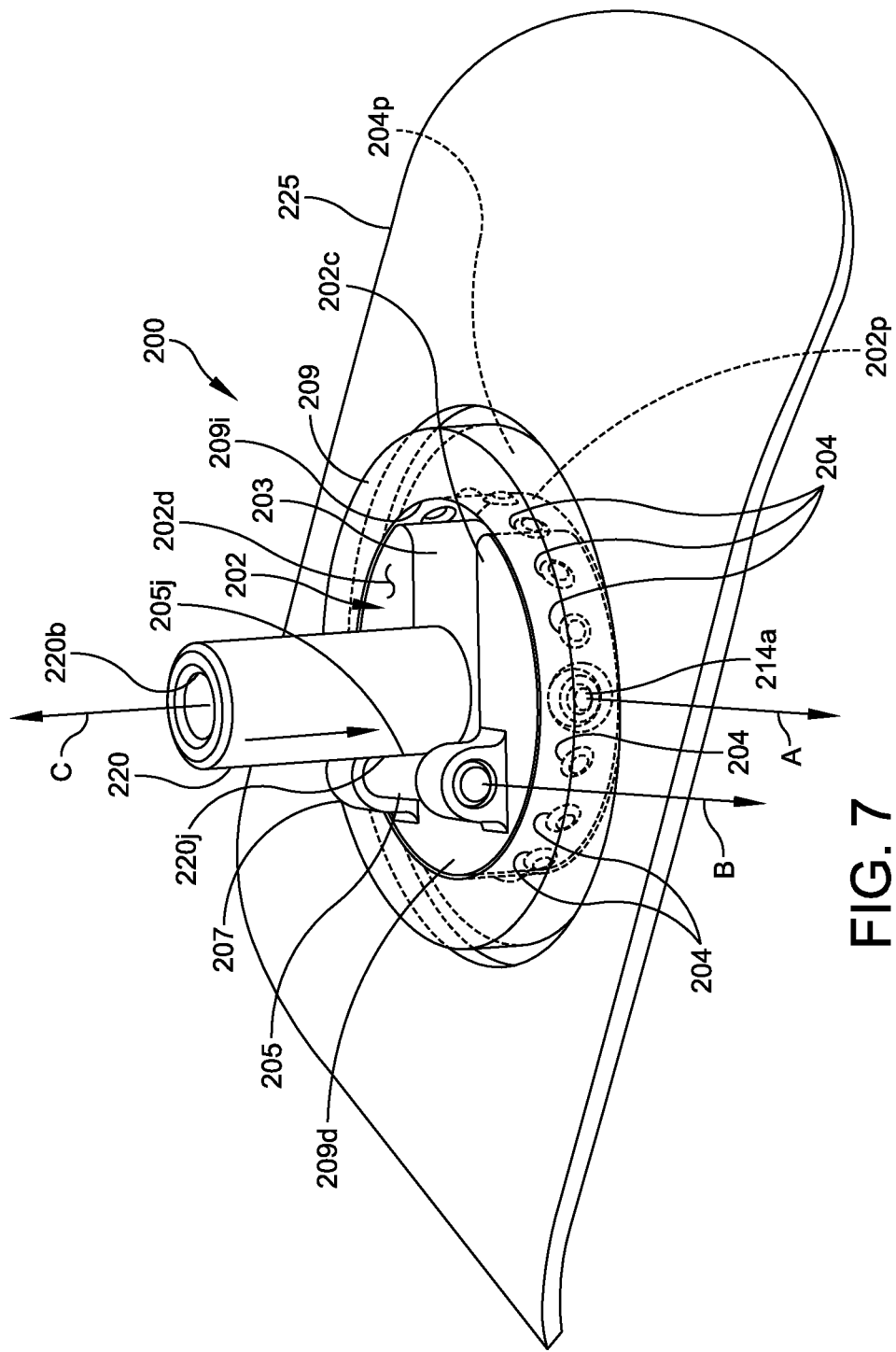
FIG. 7 is an isometric view of a second exemplary embodiment of a guide.

FIGS. 7-9 show an alternative embodiment of a guide 200 for a bone cut, comprising a guide base 209 having an inner wall 209i defining an opening. The inner wall 209i has a plurality of detents 204 distributed around the opening. The guide base 209 has a proximal surface 209p adapted to contact the skin of a person, and a distal surface 209d opposite the proximal surface 209p. The distal surface 209d is adapted to face away from the skin when the proximal surface 209p of the guide base 209 contacts the skin.

An inner collar 202 has a pair of spring loaded devices (e.g., ball plungers or blade plungers) 214a, 214b extending outward therefrom in opposite directions. The central axes of the spring loaded devices 214a, 214b both lie along an axis A. The inner collar 202 is mountable with the pair of spring loaded devices 214a, 214b fitting within two of the plurality of detents 204. The inner collar 202 can be rotated around an axis C normal to the plate 225, so the spring loaded devices 214a, 214b fit into a different pair of detents 204 in the inner surface 209i of the guide base 209. (When the inner collar 202 is in the position shown in FIGS. 7 and 8, the central axis of the sleeve 220 coincides with the axis C.) Thus, the inner surface 209i with detents 204 act as a circular track having a predetermined number of discrete positions (corresponding to the detents 204) in which the spring loaded devices 214a, 214b can be positioned. By rotating the inner collar 202 within the guide base 209 about the axis C, the surgeon can manipulate the angle between the cuts of the chevron osteotomy.

Note that the inner collar 202 rotates about the axis C, but the distal surface 202d remains in the same plane when the sleeve 220 and pin 205 pivot relative to the axis C. The inner collar 202 does not pivot around the axis A of the spring loaded devices 214, 214b in clinical use. The sleeve 220 can pivot without causing the inner collar 202 to pivot or move.

The inner collar 202 has a rotatable pin 205 mounted in knuckles 207. The pin 205 has a central axis B in a plane parallel to a plane containing the central axis A of the spring loaded devices 214a, 214b. For example, in the position shown in FIGS. 7-9, if the central axis A of the spring loaded devices 214a, 214b is oriented in a horizontal plane, the axis B of the pin 205 is also in a horizontal plane. In some embodiments, the axis B is parallel to the axis A. In other embodiments, the axes A and B are located in parallel planes, but are not parallel to each other, i.e., the axes A and B can be skewed.

The inner collar 202 has a sleeve 220 attached to the pin 205 (by welding, brazing, casting, or additive manufacturing, for example). The sleeve 220 has an inner wall 220b defining the bore of the inner collar 202, for receiving the cutting tool 130. The cutting tool 130 can rotate freely within the bore 220b of the sleeve 220.

The inner collar 202 has a slot 203 extending inward from the circumference of the inner collar 202. The slot penetrates from the distal surface 202d of the inner collar to the proximal surface 202p of the inner collar 220. The inner collar 202 is adapted to sweep the cutting tool 130 along the slot 203 when the sleeve 220 and cutting tool 130 rotate about the pin 205 from the position of the cutting tool 130 in FIG. 8 to the position of the cutting tool 130 in FIG. 9. As noted above, the sleeve 220 is fixed to the pin 205. When the pin 205 rotates, the sleeve 220 revolves around the pin 205 causing the cutting tool 130 to pivot and sweep across the length of the slot 203. Note that the position of the inner collar 202 is the same in FIGS. 8 and 9, whereas the sleeve 220, pin 205 and tool 130 pivot about the pin 205, so that the cutting tool 130 moves within a plane normal to the central axis B of the pin 205. The inner collar 202 is configured to pivot the cutting tool 130 about the axis B, for cutting a bone. In some embodiments, the axis B lies along or parallel to the axis A, along which the spring loaded devices 214a, 214b lie.

In operation, the guide 200 is positioned on the patient's body, and the plate 225 or the proximal surface 209p of guide base 209 is adhered to the body near the wound site. The inner collar 202 is rotated about the axis C to one of the positions where the spring loaded devices 214a, 214b engage two of the detents 204 on opposite sides of the inner surface 209i of the guide base 209, and the slot 203 is aligned with the location of the desired cut. The tool 130 is inserted through the bore 220b of the sleeve 220 and rotated or oscillated to cut or grind the bone the tool 130 contacts. The sleeve 220 is revolved around the pin 205 to sweep the tool 130 from the position of FIG. 8 to the position of FIG. 9, cutting the bone.

Figure 12A:
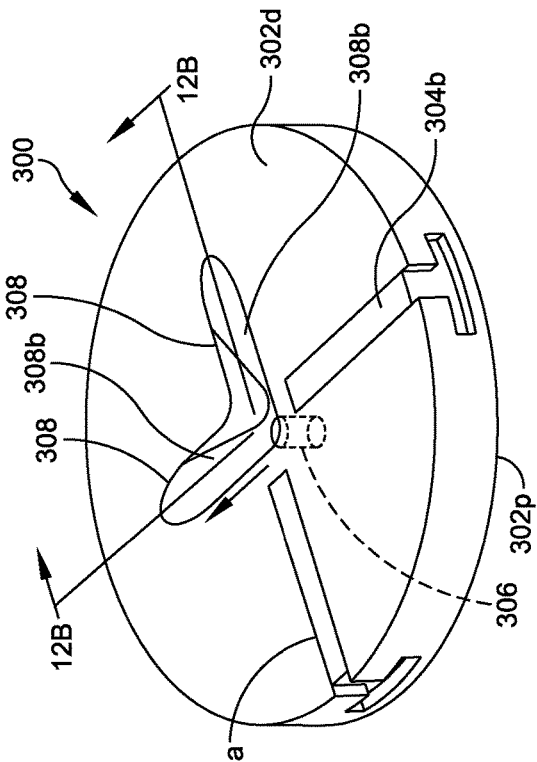
FIGS. 10-12B show a third exemplary embodiment of a guide configured to perform cuts with a fixed chevron angle.
Figure 12B:
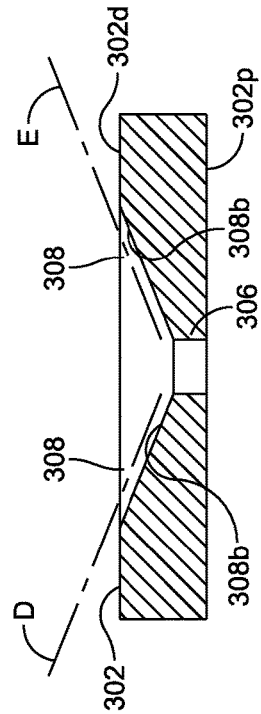
Figure 10:
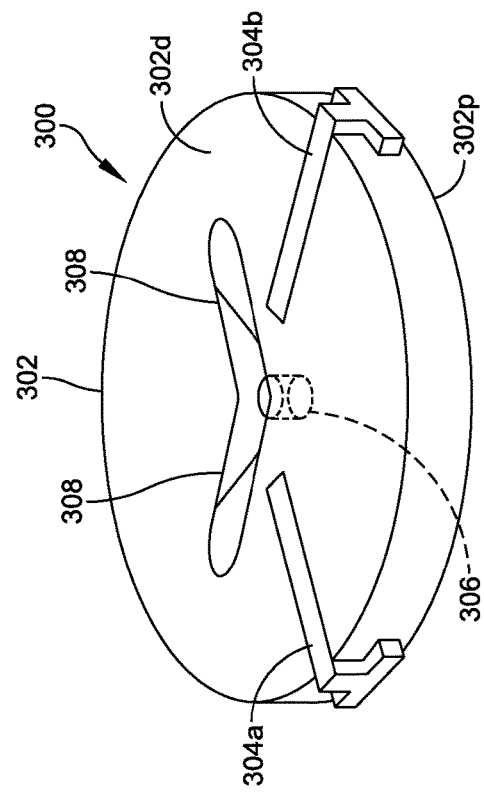
Figure 11:
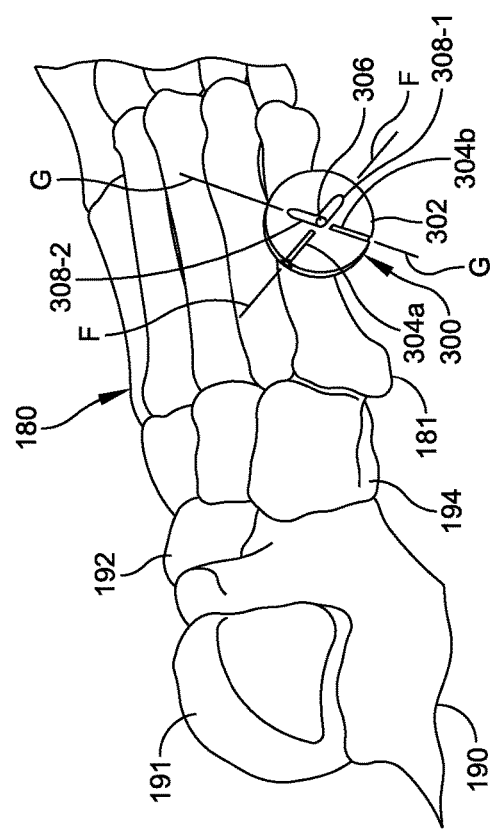

FIGS. 10-12B show an embodiment of a guide 300 for providing a fixed predetermined angle between bone cuts. There are a plurality of angled features representing a chevron. FIGS. 10 and 11 are isometric views showing a guide 300 having an angle from about 120° to about 150° between cuts. FIGS. 12A and 12B show an otherwise similar guide 300 having different angles. Other embodiments (not shown) can have angles of less than 120° (e.g., about 90° to 119°) between cuts. In some embodiments, a kit includes a plurality of guides 300, each guide having a respectively different angle between cuts.

The guide 300 can include a body 302, which may be in the form of a disk or cylinder. The body 302 has a proximal surface 302p adapted to contact the skin of a person, and a distal surface 302d opposite the proximal surface. The distal surface 302d has one or more distal channels 308. Each distal channel 308 has a respective longitudinal axis D and E (FIG. 12B) forming an oblique angle with the distal surface 302d. Each distal channel 308 has a bottom surface 308b extending partially around the respective longitudinal axis thereof, each distal channel extending from the bottom surface 308b to the distal surface 302d, so each distal channel 308 has a varying depth.

A central longitudinal bore 306 extends through the body 302, from the proximal surface 302p to the respective bottom surface 308b of each respective distal channel 308. The central longitudinal bore 306 is adapted to receive a drilling or cutting tool 130 (shown in FIG. 4) therethrough. The body 302 further comprises one or more radiopaque markers 304 on or in the distal surface 302d. Each respective marker 304 is aligned with a projection of a respective one of the one or more distal channels 308 on the distal surface 302d. For example, as best seen in FIG. 11, one marker 304a and a respective channel 308-1 lie along the same line F, and the other marker 304b and other channel 308-2 lie along the same line G.

The body 302 can be mounted to the patient's body (e.g., foot) using an adhesive (e.g., a pressure-sensitive adhesive) on the proximal surface 302p. The surgeon aligns the markers 304 with the planes of the desired cuts, and presses the guide 300 into place. The cutting tool 130 in inserted through the central longitudinal bore 306, and cutting or grinding begins by rotating the tool 130 about its longitudinal axis. The proximal end 134 of the tool 130 is tilted toward the channel 308 along the line F or G of the desired cut, and the cutting edges 132 sweep along the path of the cut, in the plane of the radiopaque marker 304 opposite the channel 308 toward which the top portion 134 moves.

Although the body 302 in FIGS. 10-12 is a cylinder having a small aspect ratio between body height and body diameter (i.e., a disk), other embodiments have different aspect ratios. For example, in other embodiments, the height of the body 302 can be as large as, or larger than, the diameter of the body 302.

Further, in other embodiments, the body 302 is not a cylinder, but a prism with polygonal top and bottom surfaces. For example, the body 302 can be an octagonal prism (not shown). In some embodiments, the body 302 is a prism (not shown) having at least as many sides as the number of markers. In some embodiments, the body 302 is a prism (not shown) having the same number of sides as the number of markers 304, and each marker extends to a respective corner of the distal face of the prism.

Figure 13:
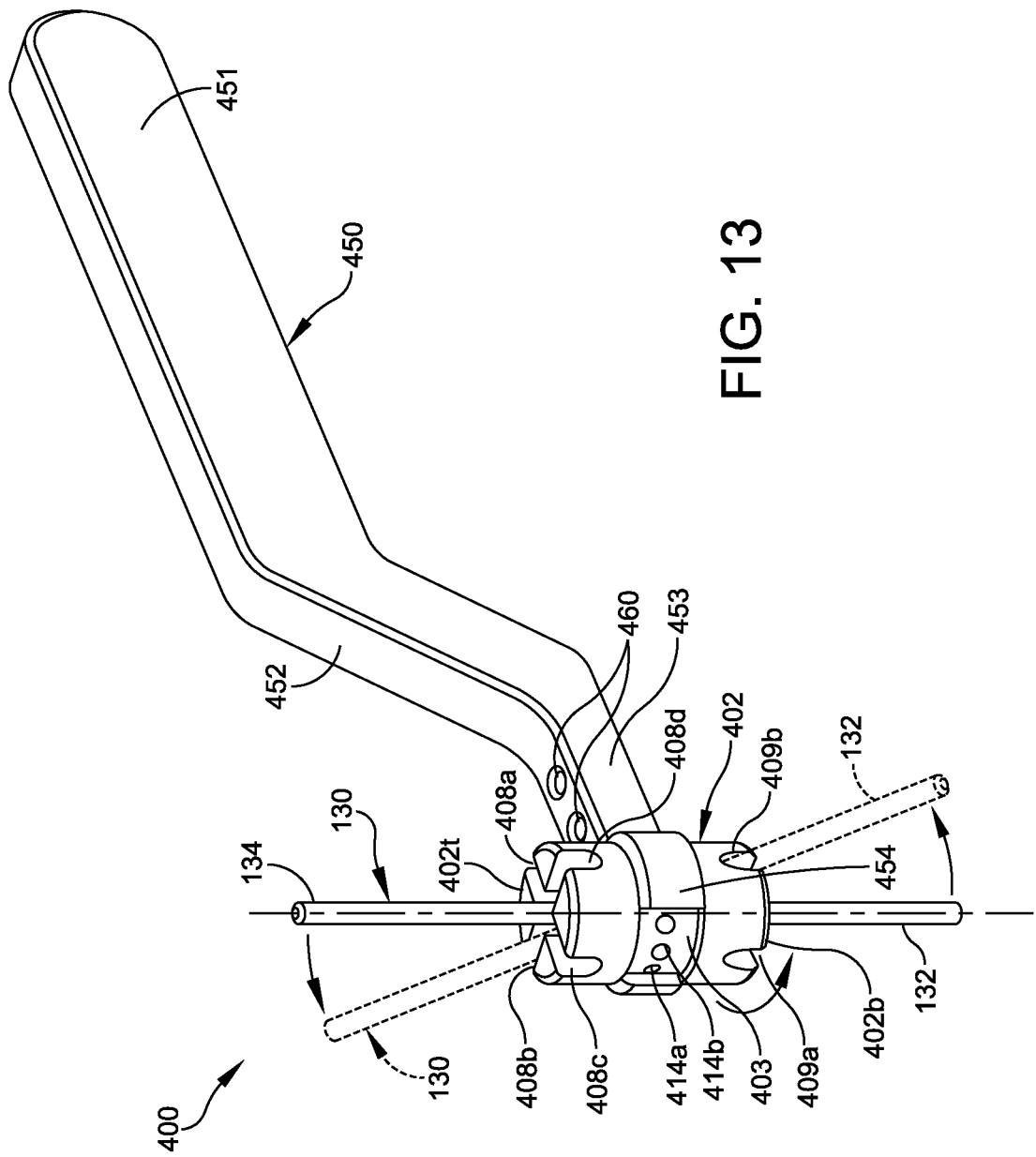
FIG. 13 shows a variation of the guide of FIG. 10, having a handle.

FIGS. 13-18 show variations of the guide 300 of FIGS. 10-12. The guide 400 of FIGS. 13 and 14 includes a body 402 and further includes a handle 450. The body 402 has a top (distal) surface 402t and a bottom (proximal) surface 402b. The distal surface 402t has one or more distal channels 408a-408d. Each distal channel 408a-408d has a corresponding diagonally opposed proximal channel 409a-409d on the proximal surface 402b. The proximal channels 409a-409d and the corresponding distal channel 408a-408d thereof are adapted to receive the drilling or cutting tool 130 simultaneously while the drilling or cutting tool 130 is oriented at an oblique angle relative to the distal surface. For example, as shown in FIG. 13, when the proximal end 134 of the tool 130 tilts into the channel 408b, the cutting edge 132 of the tool 130 tilts into the corresponding diagonally opposed proximal channel 409b on the proximal surface 402b of the body 402, as shown in phantom.

In some embodiments, the side surface 403 of the body 402 has a plurality of detents 414a, 414b, . . . The detents 414b, 414b, . . . are configured to receive a ball or blade plunger (not shown in FIG. 13) extending inwardly from an external device. In other embodiments, the body 402 has one or more spring loaded devices (not shown in FIG. 13 or 14), and the detents are included in the external device.

In the examples, the exemplary handle 450 has a (first) gripping section 451, a (second) offset section 452 and a (third) alignment section 453. The gripping section 451 can have any shape adapted to be gripped securely by the surgeon. The offset section 452 provides sufficient clearance for the surgeon's hand to fit between the patient's body and the gripping section 451 of the handle 450. The alignment section 453 has surfaces defining one or more alignment apertures 460 near the holder, the one or more apertures extending from a proximal side of the handle to a distal side of the handle adapted to receive fixation elements (e.g., alignment wires, such as k-wires or pins).

The handle 450 has a holder 454 at one end thereof, adapted to attach to a side surface 403 of the body 402, between the proximal surface 402*b* and the distal surface 402*t* of the body 402. For example, the holder 454 can be attached to the end of the alignment section 453. In some embodiments, the holder 454 at least partially surrounds the side surface 403. Although the exemplary holder 454 is configured to grip the side surface 403 of the body 402, in other embodiments (not shown), the holder 454 is configured to attach to the top surface 402*t* or the bottom surface 402*b* of the body.

In some embodiments, the holder 454 has one or more spring loaded devices extending radially inward. For example, a ball plunger (hidden in FIG. 13) can extend in the longitudinal direction of the handle, with the ball thereof protruding from the holder 454. The ball of the ball plunger is configured to fit into one of the one or more detents 414*a*, 414*b*, . . . in the side surface 403 of the body 402.

Although the holder 454 is in the form or a pair of thin, curved plates, in other embodiments (not shown), the holder plates have a radial thickness sufficient to hold two or more spring loaded devices within the holder. The two or more spring loaded devices can fit into two or more of the plurality of detents 414*a*, 414*b*, . . . in the guide body 402, where each detent 414*a*, 414*b*, . . . is adapted to receive a respective ball or blade of each of the one or more spring loaded devices.

In another embodiment (not shown) the guide body 402 has one or more spring loaded devices extending radially outward from the side surface 403, and the holder 454 has one or more detents (not shown in FIG. 13 or 14) adapted to receive a ball or blade of a respective one of the one or more spring loaded devices.

In use, the surgeon inserts the guide body 402 into the handle 450, rotating the guide body until the spring loaded devices engage respective detents 414*a*, 414*b*, . . . Holding the gripping section 451, the surgeon positions the guide body 402 to align one of the channels 408*a*-408*d* with the plane of the desired cut. The surgeon inserts fixation elements (e.g., k-wires, not shown) into the apertures 460. With the k-wires in place, the surgeon inserts the tool 130 through the central longitudinal bore (not shown) of the body 402, as shown in FIG. 13.

Figure 15:
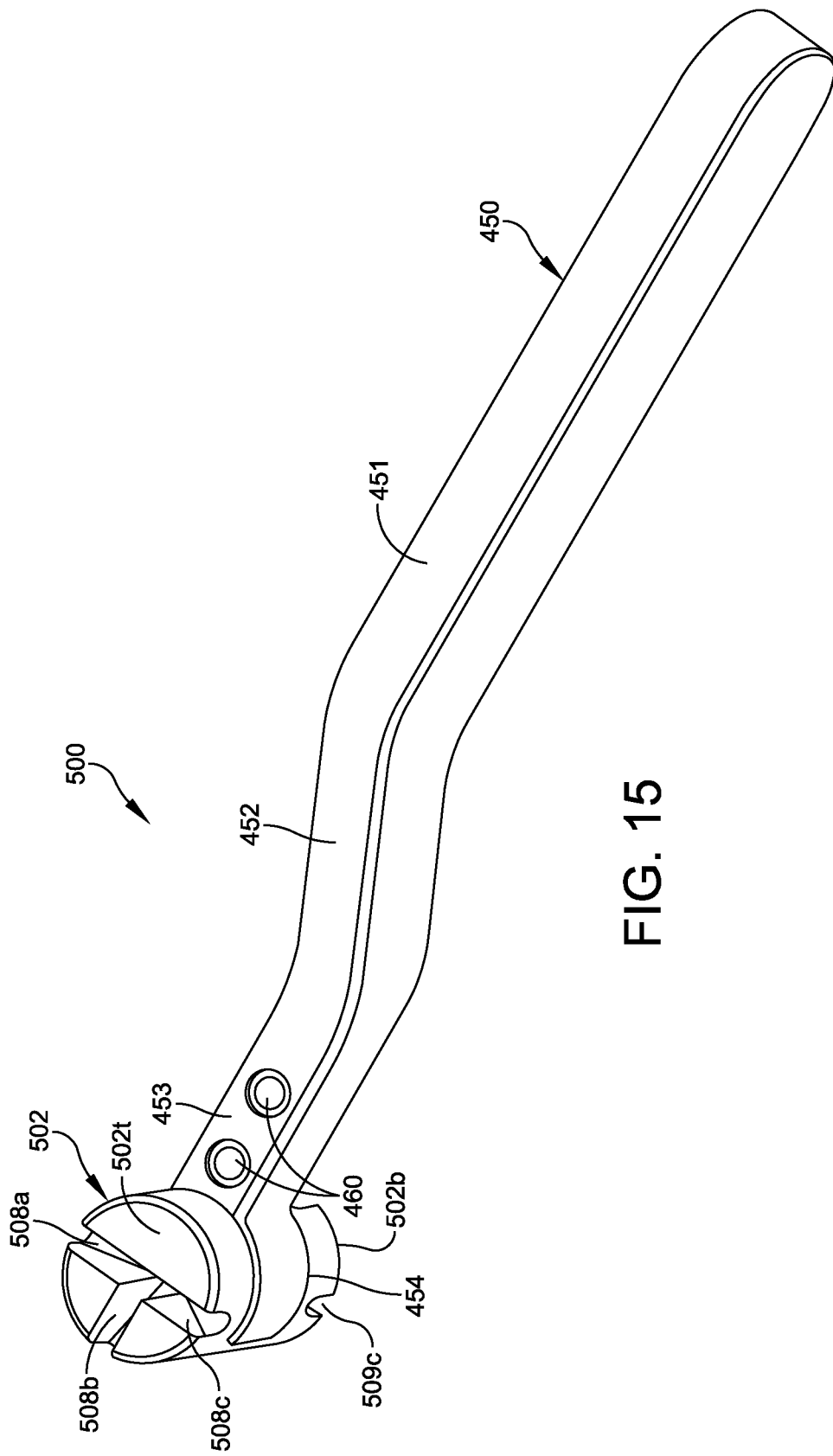

FIG. 15 shows a variation of the guide 500 including a guide body 502, having three distal channels 508*a*-508*c* arranged at 0°, 90°, and 180° around the circumference of the body 502. Each of the distal channels 508*a*-508*c* has a corresponding diagonally opposed proximal channel 509*a*-509*c* on the proximal surface 502*b*. The proximal channels 509*a*-509*c* and the corresponding distal channel 508*a*-508*c* thereof are adapted to receive the drilling or cutting tool 130 simultaneously while the drilling or cutting tool 130 is oriented at an oblique angle relative to the distal surface 502*t*.

Figure 14:
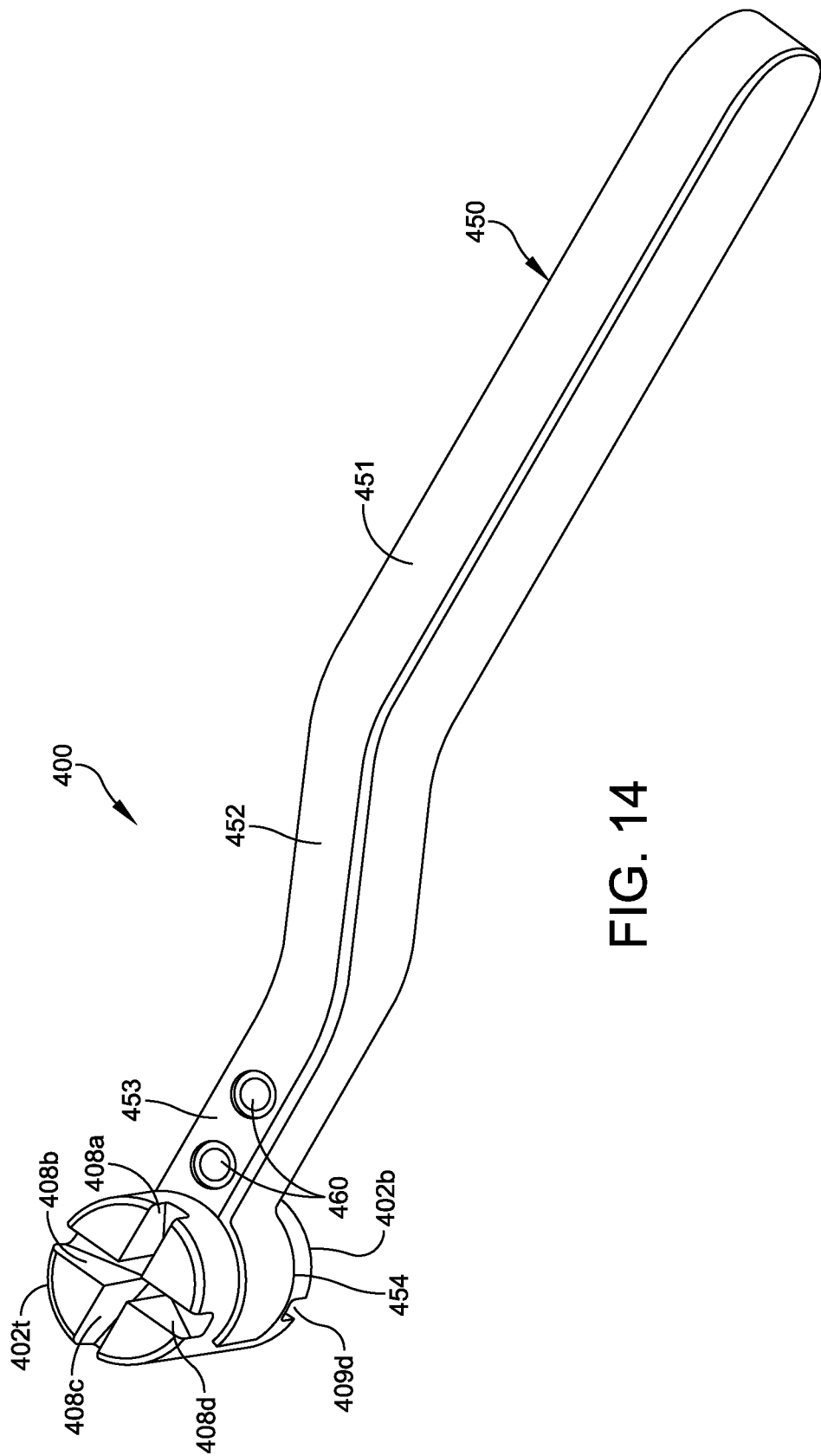
FIGS. 14-18 show variations of the guide of FIG. 13, having different numbers of channels.

The guide 500 further includes a handle, which can be the handle 450 shown in FIGS. 13 and 14. For brevity, a description of the handle 450 is not repeated.

Figure 16:
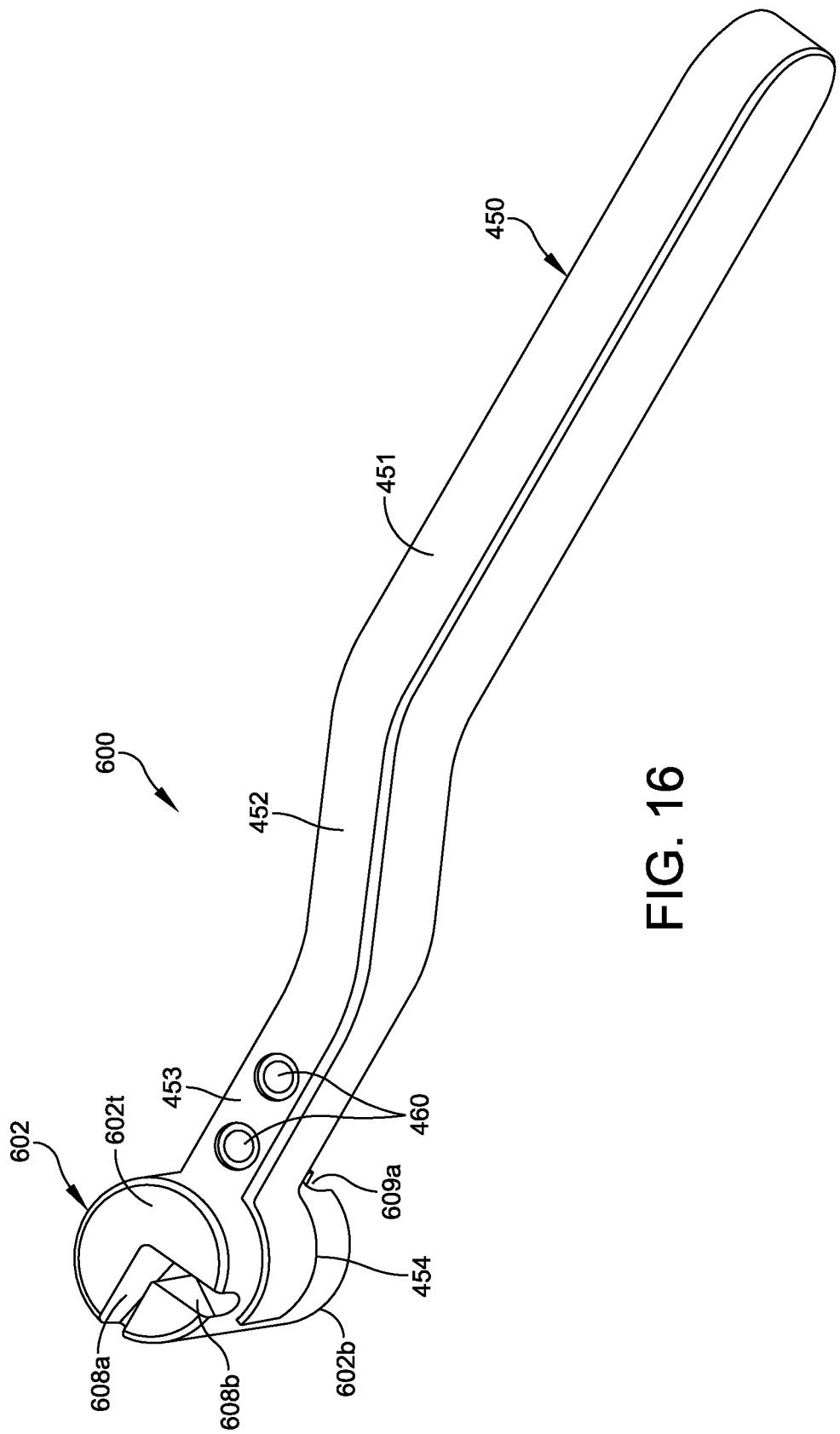

FIG. 16 shows a variation of the guide 600 including a guide body 602, having two distal channels 608*a* and 608*b* arranged at 0° and 900 around the circumference of the body 602. Each of the distal channels 608*a*-608*b* has a corresponding diagonally opposed proximal channel 609*a*-609*b* on the proximal surface 602*b*. The proximal channels 609*a*-609*b* and the corresponding distal channel 608*a*-608*b* thereof are adapted to receive the drilling or cutting tool 130 simultaneously while the drilling or cutting tool 130 is oriented at an oblique angle relative to the distal surface 602*t*.

The guide 600 further includes a handle, which can be the handle 450 shown in FIGS. 13 and 14. For brevity, a description of the handle 450 is not repeated.

Figure 17:
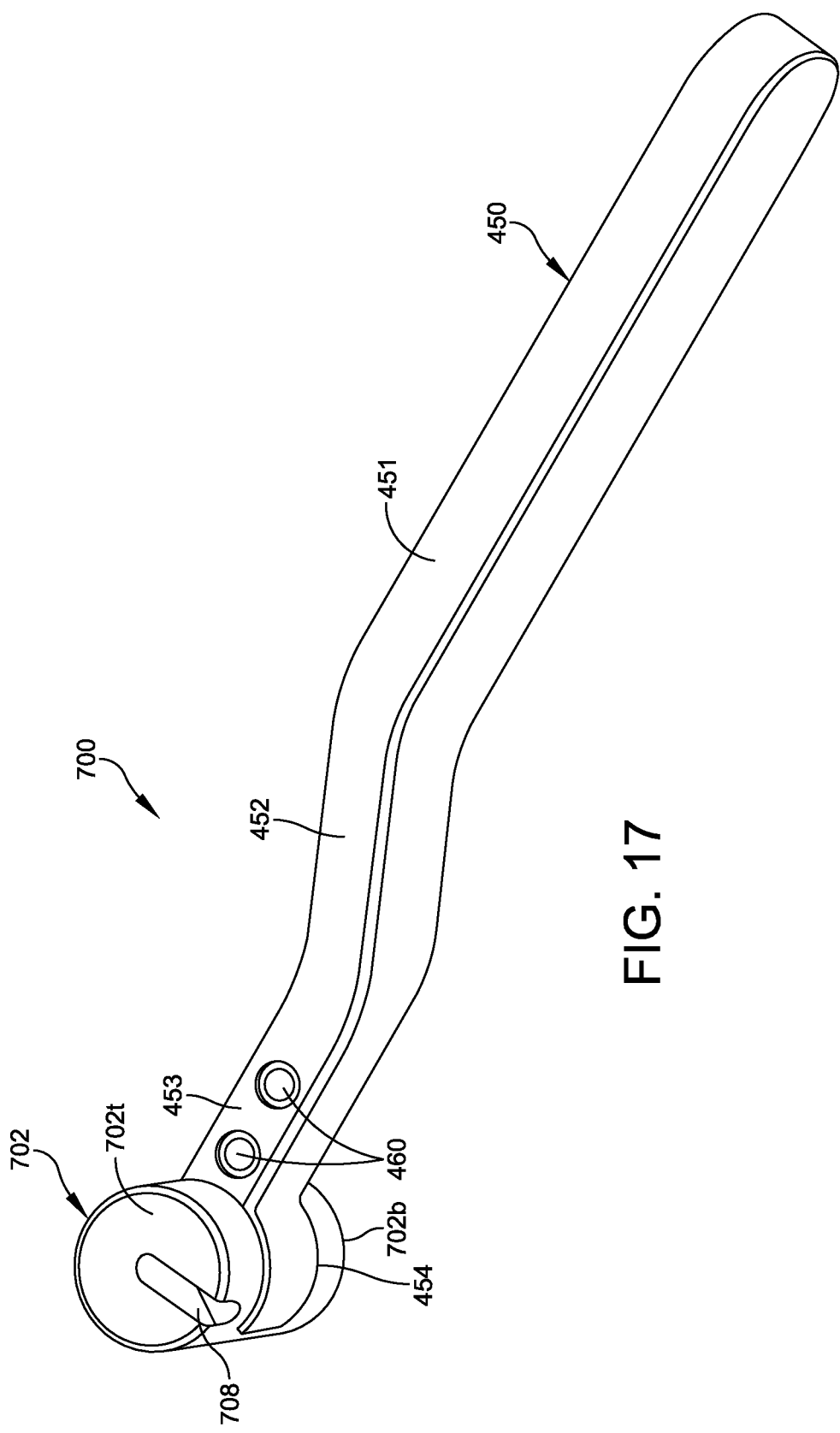

FIG. 17 shows a variation of the guide 700 including a guide body 702, having a single distal channel 708. The distal channel 708 has a corresponding diagonally opposed proximal channel (not shown in FIG. 17) on the proximal surface 702*b*. The distal channel 708 and the corresponding proximal channel thereof are adapted to receive the drilling or cutting tool 130 simultaneously while the drilling or cutting tool 130 is oriented at an oblique angle relative to the distal surface 702*t*.

The guide 700 further includes a handle, which can be the handle 450 shown in FIGS. 13 and 14. For brevity, a description of the handle 450 is not repeated.

Figure 18:
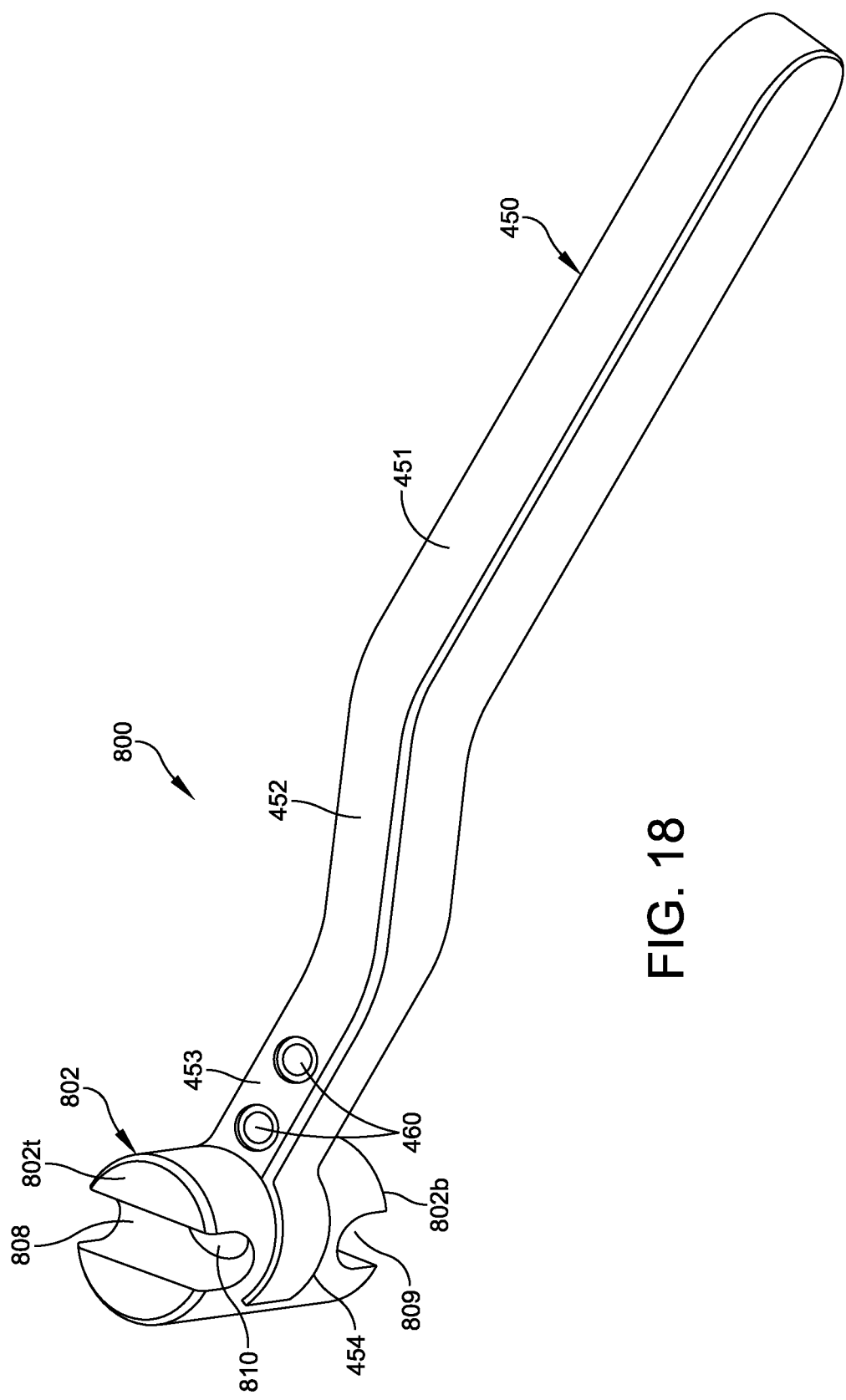
Figure 19:
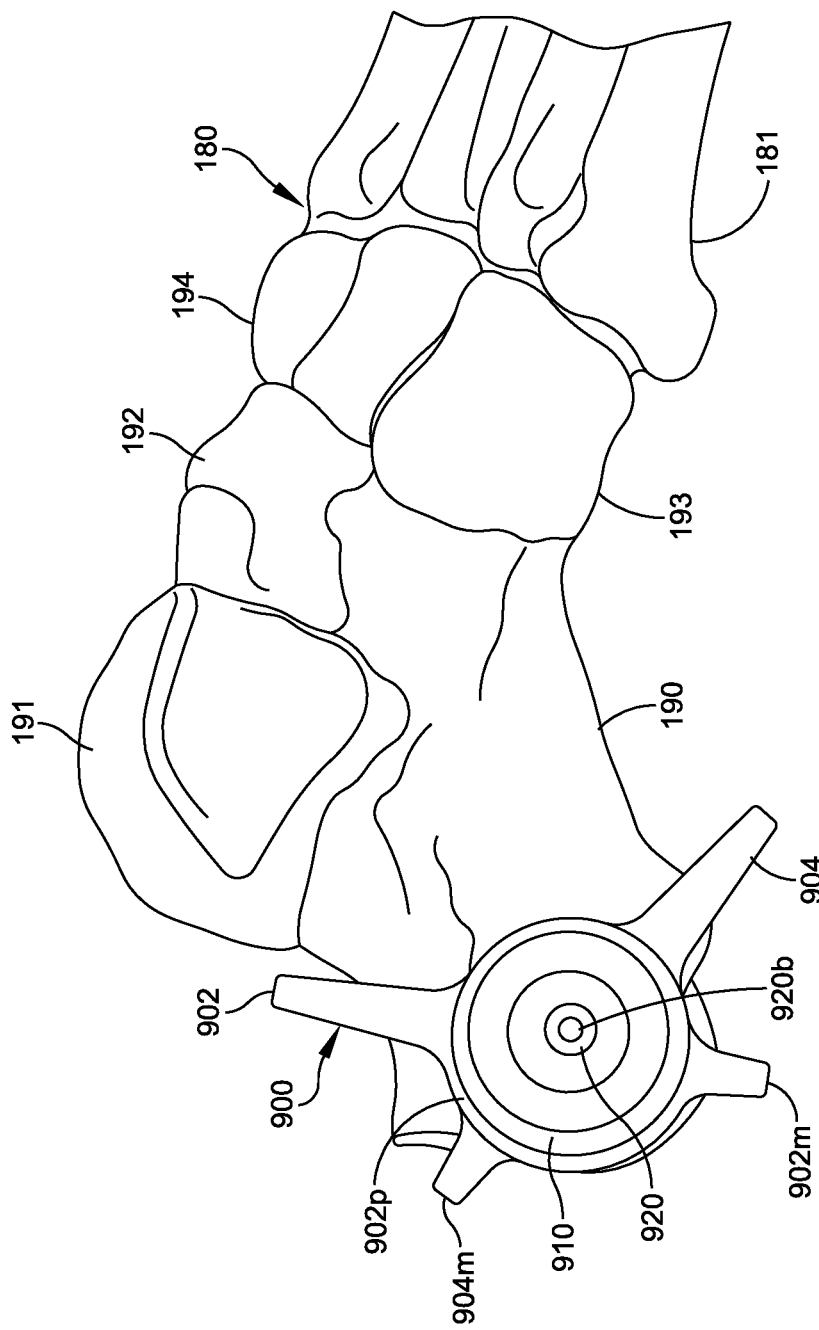
FIG. 19 is an isometric view of a fourth exemplary embodiment of the guide adhered to a bone.

FIG. 18 shows a variation of the guide 800 including a guide body 802, having an extended channel 808 extending across a diameter of the body 802. The distal channel 808 has a corresponding proximal channel 809 on the proximal surface 802*b*. The proximal channel 809 and the corresponding distal channel 808 thereof are adapted to receive the drilling or cutting tool 130 simultaneously while the drilling or cutting tool 130 sweeps through an angle from $-\alpha$ to $+\alpha$ relative to the normal of distal surface 802*t*, where $\alpha$ can be an angle from 0° to about 60°. In some embodiments, $\alpha$ can be an angle from 0° to about 45°.

The guide 800 further includes a handle, which can be the handle 450 shown in FIGS. 13 and 14. For brevity, a description of the handle 450 is not repeated.

FIGS. 19-23 show an embodiment of a guide 900 for an osteotomy, comprising a circular body 901 having at least one circular groove 912 (FIG. 20) on an outer side surface thereof and an inner channel 913 on the inner surface thereof. In some embodiments, the body 901 comprises an annular portion 910 having a T-shaped cross-section (which may be the distal portion) and a portion 911 in the form of an annular disk (which may be the proximal portion), as best seen in FIG. 23). In other embodiments (not shown) the proximal portion has a T-shaped cross section, and the distal portion is an annular disk. In an alternative embodiment, both the annular portions 910 and 911 can be T-shaped in cross-section, such that the vertical portions of each T meet.

The guide 900 includes a first arm 902 and a second arm 904 extending radially away from the circular body 901. At least one of the first arm 902 or the second arm 904 is movable relative to the other of the first arm 902 or second arm 904 to vary an angle between the first arm 902 and the second arm 904. For example, in FIG. 19, the first arm 902 and second arm 904 are about 120° apart. In some embodiments, the first arm 902 and second arm 904 comprise a radiopaque material.

Some embodiments further comprise a first ring or plate 902*p* having an inner diameter thereof adapted to fit around the at least one circular groove 912. The first arm 902 extends radially from the first ring or plate 902*p*. A first marker 902*m* extends radially from the first ring or plate 902*p* in the opposite direction from the first arm 902. In some embodiments, the first ring or plate 902*p*, the first arm 902 and the first marker 902*m* are all formed from a single piece of material. A second ring or plate 904*p* has an inner diameter thereof adapted to fit around the at least one circular groove 912. The second arm 904 extends radially from the second ring or plate 904*p*. A second marker 904*m* extends radially from the second ring or plate 904*p* in the opposite direction from the second arm 904. In some embodiments, the second ring or plate 904*p*, the second arm 904 and the second marker 904*m* are all formed from a single piece of material. In some embodiments, each of the first ring or plate 902*p* and second ring or plate 904*p* are rotatable to move the first arm 902 or second arm 904 respectively. By rotating one or both of the first ring or plate 902*p* and second ring or plate 904*p*, the angle between the first arm 902 and second arm 904 can be adjusted.

In some embodiments a washer or spacer (not shown) can be inserted between the first ring or plate 902*p* and second ring or plate 904*p*. In some embodiments, a second washer can be inserted on the distal side of the first ring or plate 902*p*, between first ring or plate 902*p* and the distal portion 910. In some embodiments, a third washer can be inserted on the proximal side of the second ring or plate 904*p*, between second ring or plate 904*p* and the proximal portion 911.

A sleeve 920 is concentrically arranged inside the body 901. The sleeve 920 has an inner surface defining a bore 920*b* through the sleeve 920. The bore 920*b* is adapted to receive a cutting or grinding tool 130 therethrough. As best seen in FIG. 23, the sleeve 920 has a plurality of pegs 921, 922, which are retained within an inner groove 913 of the body 901. In some embodiments, the sleeve 920 comprises a radiopaque material.

In some embodiments, to assemble the guide 900, the sleeve 920 is inserted into the inner channel 913 of the annular distal portion 910, and the first ring or plate 902*p* and second ring or plate 904*p* are placed in the groove 912 radially outward of the vertical portion 915 of the T-shaped distal portion 910. The proximal portion 911 then engages the distal portion 910, enclosing the pegs 921, 922 in the inner channel 913, and the first arm 902, and second arm 904 in the circular groove 912. The distal portion 910 and proximal portion 911 of the body 901 can be joined by threads, adhesive, soldering, or welding, for example. This construction allows the first arm 902, and the second arm 904 to pivot independently of each other, to achieve any desired angle therebetween for guiding a chevron osteotomy.

Figure 20:
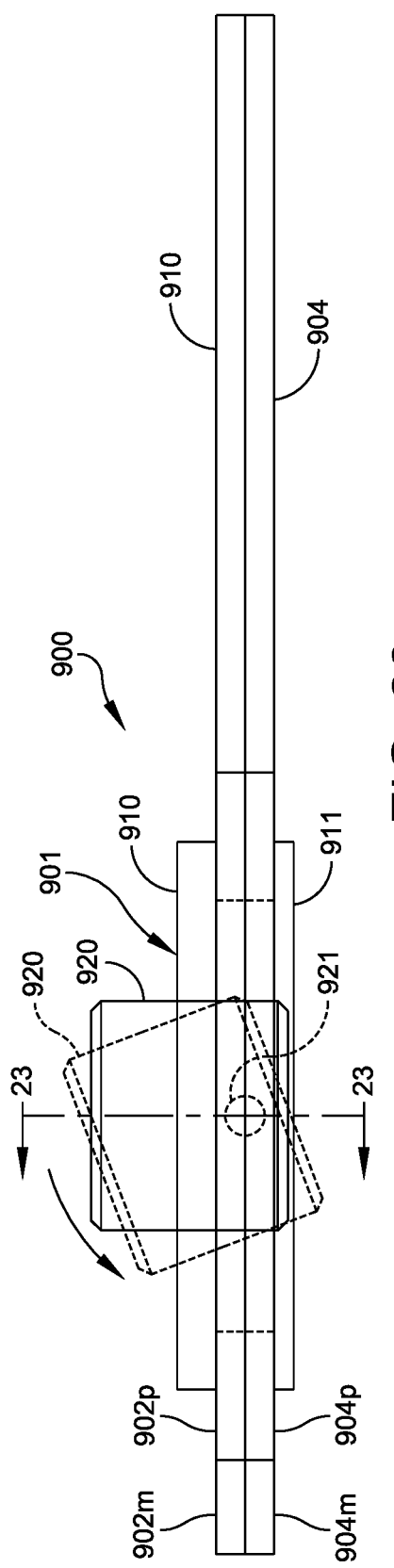
FIG. 20 is a side view of the guide of FIG. 19, where the tilted position of the sleeve is indicated by dashed lines.
Figure 21:
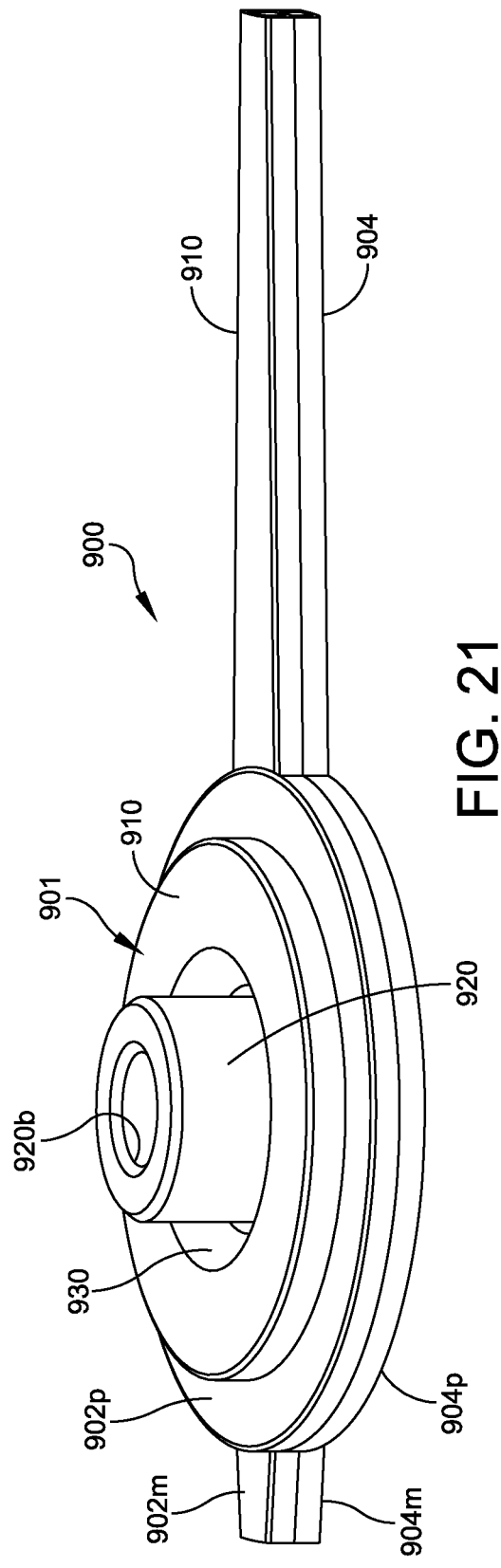
FIG. 21 is a top isometric view of the guide of FIG. 19.

The sleeve 220 can rotate about the central axis H (FIG. 23) within the inner channel 913. In some embodiments, the outer diameter of the sleeve 220 is smaller than the inner diameter of the proximal portion 911 or the horizontal part of the distal portion 910, providing a cylindrical annular clearance 930 to allow the sleeve 220 to pivot around a central axis J of the pegs 921, 922. For example, FIG. 20 shows the sleeve 920 in its tilted position in phantom. By tilting the sleeve 920 about the axis J of the pegs 921, 922, the guide 900 can sweep the cutting portion 132 of the cutting tool 130 across the path of the desired cut. The surgeon can align the arms 902 and 904 with the desired cut planes.

In some embodiments, the first ring or plate 902*p* and second ring or plate 904*p* have markers or extensions 902*m* and 904*m*, respectively, diametrically opposite the arms 902 and 904, respectively. The surgeon can rotate the sleeve 920 about the axis H until a selected one of the arms 902 or 904 is 90 degrees from peg 921 and 90 degrees from peg 922. (For example, the sleeve 920 can have a mark or indicia 90 degrees from peg 921 and 90 degrees from peg 922, which the surgeon can align with the selected one of the arms 902, 904.) The surgeon can then insert the cutting tool and pivot the cutting tool 130 and sleeve 920 about the pegs 921, 922, so the top portion 134 of the tool approaches the marker or extension 902*m* or 904*m* corresponding to the selected arm 902 or 904, and the cutting portion 132 sweeps along the desired cut plane aligned with the selected arm 902 or 904. The radial distance between the outer diameter of the sleeve 920 and the inner diameter of the body 901 can be selected to control the maximum tilt angle about the axis J, so the body 901 acts as a stop to define the end of the cut.

FIGS. 24-27 show another embodiment of a guide 1000 for cutting a bone. The guide 1000 includes a cylindrical body 1002 having a proximal surface 1004 adapted to contact a skin of a person. The proximal surface 1004 has a proximal chamfer 1005 at a center thereof. The guide 1000 has a distal surface 1006 opposite the proximal surface 1004. The distal surface 1006 having a distal chamfer 1007 at a center thereof. The cylindrical body 1002 has an inner wall defining a central longitudinal bore 1008 extending through the body 1002 from the proximal chamfer 1005 to the distal chamfer 1007. The central bore 1008 is adapted to receive a drilling or cutting tool 1030 (FIG. 27) therethrough.

Figure 26:
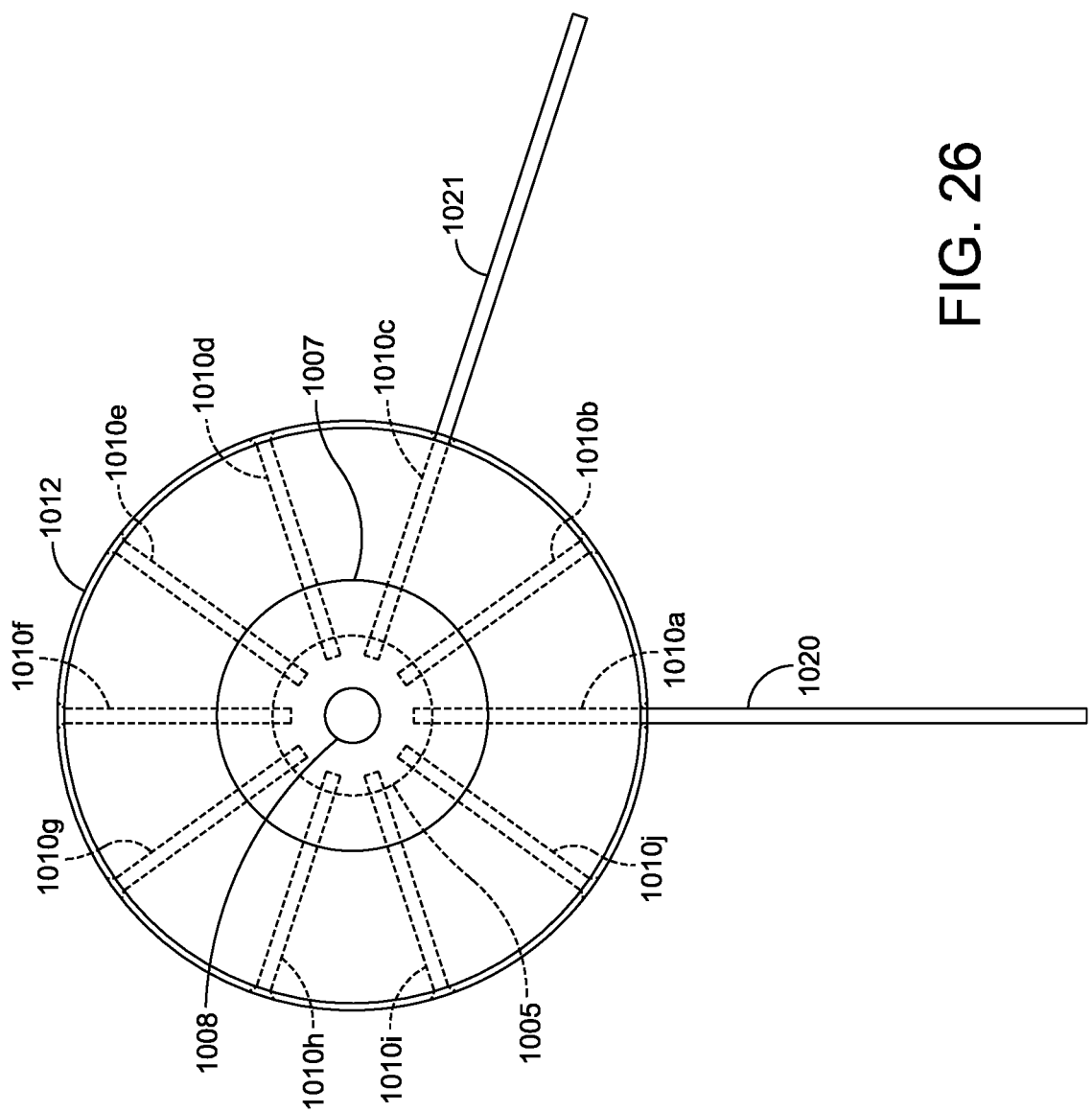
FIG. 26 is a plane view of the guide of FIG. 24 with k-wires inserted therein.

The cylindrical body 1002 has a circumferential surface 1012 with a plurality of radial bores 1010*a*-1010*j* (FIG. 26) extending inward from the circumferential edge 1012. The radial bores 1010*a*-1010*j* are adapted to receive fixation elements 1020, 1021 (FIG. 26). Although the exemplary guide 1000 has ten radial bores 1010*a*-1010*j*, other embodiments of the guide can include any desired number of radial bores. Although the exemplary guide 1000 has radial bores 1010*a*-1010*j* evenly spaced 36° apart from each other, the spacing between bores can vary within a single guide. For example, in one embodiment, some of the angles between adjacent bores are 36°, and some of the angles between bores are 18°. This is just one example, and a given guide can have more than two different angles between respective pairs of adjacent bores.

In some embodiments, the body 1002 comprises a radiolucent material, and the fixation elements comprise a radiopaque material, such as stainless steel. In some embodiments, the fixation elements 1020, 1021 are k-wires or the like. This allows the surgeon to view and align the fixation elements 1020, 1021 with the desired cut plane using fluoroscopy during surgery.

In some embodiments, the body 1002 comprises a pressure-sensitive adhesive 1014 on a peripheral portion (e.g., near the peripheral edge 1012) of the proximal surface 1004. For example, the pressure-sensitive adhesive 1014 can be applied in an annular ring near the circumference of the peripheral surface 1004 of body 1002, or adhesive 1014 can be applied in a plurality of discrete areas. The pressure-sensitive adhesive 1014 can be covered with release-coating papers prior to use.

To use the guide 1000, the surgeon determines which chevron angle is appropriate for the patient's osteotomy, and selects two radial bores (e.g., 1010*a* and 1010*c*) separated by the desired chevron angle. The surgeon inserts two fixation elements (e.g., k-wires 1020, 1021) into the selected radial bores. Using fluoroscopy, the surgeon can align the guide 1000 with the patient's bones, remove the release-coating papers from the pressure-sensitive adhesive 1014, and affix the guide 1000 to the patient's skin, outside the incision. The surgeon can then insert the cutting tool or burr 1030 through the central longitudinal bore 1008 of the body 1002. The surgeon can sweep the cutting tool or burr 1030 across the cut planes defined by the fixation elements 1010*a*, 1010*c* to cut the desired portion of bone(s). The proximal chamfer 1005 and distal chamfer 1007 allow the cutting tool or burr 1030 to pivot within the central longitudinal bore 1008.

The guides described herein provide the surgeon with physical cues for forming chevron-shaped osteotomies in bones. The guides can be used to physically restrict the angle of the cutting tool to a desired plane when performing a cut, reducing the risk of skin or soft tissue damage. As the cutting tool is tilted to sweep across the cut plane, various embodiments of the guide can provide a stop at a desired end of the cut.

Although the subject matter has been described in terms of exemplary embodiments, it is not limited thereto. Rather, the appended claims should be construed broadly, to include other variants and embodiments, which may be made by those skilled in the art.

What is claimed is:

1. A guide for cutting a bone, comprising:
   a cylindrical body having:
   a proximal surface adapted to contact a skin of a person, the proximal surface having a proximal chamfer at a center thereof,
   a distal surface opposite the proximal surface, the distal surface having a distal chamfer at a center thereof,
   the cylindrical body having an inner wall defining a central longitudinal bore extending through the body from the proximal chamfer to the distal chamfer, the central bore adapted to receive a drilling or cutting tool therethrough, and
   the cylindrical body having a circumferential surface with a plurality of radial bores extending inward from the circumferential edge, the radial bores adapted to receive fixation elements therein.

2. The guide of claim 1, wherein each of the plurality of radial bores is adapted to receive a k-wire.

3. The guide of claim 1, wherein the body comprises a radiolucent material.

4. The guide of claim 1, wherein the body comprises a pressure-sensitive adhesive on a peripheral portion of the proximal surface.

5. The guide of claim 4, wherein the pressure-sensitive adhesive is applied in an annular ring adjacent to a circumference of a peripheral surface of the body.

6. The guide of claim 5, wherein the pressure-sensitive adhesive is applied in a plurality of discrete areas of the body.

7. The guide of claim 1, comprising ten radial bores evenly spaced 36° apart.

8. The guide of claim 1, comprising a plurality of radial bores evenly spaced 36° apart and a plurality of adjacent radial bores evenly spaced 18° apart.

* * * * *